US008436045B2

(12) United States Patent
Cuevas Sánchez

(10) Patent No.: US 8,436,045 B2
(45) Date of Patent: May 7, 2013

(54) USE OF 2,5-DIHYDROXYBENZENE DERIVATIVES FOR TREATING ACTINIC KERATOSIS

(75) Inventor: Pedro Cuevas Sánchez, Madrid (ES)

(73) Assignee: AmDerma Pharmaceuticals, LLC, Bridgewater, NJ (US)

( * ) Notice: Subject to any disclaimer, the term of this patent is extended or adjusted under 35 U.S.C. 154(b) by 0 days.

(21) Appl. No.: 12/946,742

(22) Filed: Nov. 15, 2010

(65) Prior Publication Data
US 2011/0257264 A1    Oct. 20, 2011

Related U.S. Application Data

(63) Continuation of application No. 11/839,508, filed on Aug. 15, 2007, now abandoned, which is a continuation-in-part of application No. 11/506,469, filed on Aug. 16, 2006, now abandoned, which is a continuation-in-part of application No. 10/588,166, filed as application No. PCT/ES2005/070017 on Feb. 16, 2005, now Pat. No. 7,968,531.

(30) Foreign Application Priority Data

Feb. 17, 2004 (ES) .................................. 200400371
Aug. 16, 2006 (ES) .................................. 200602219
Jul. 2, 2007 (ES) .................................. 200701857

(51) Int. Cl.
*A01N 41/02* (2006.01)
*A01N 37/10* (2006.01)
*A61K 31/255* (2006.01)
*A61K 31/235* (2006.01)
*A61K 31/19* (2006.01)

(52) U.S. Cl.
USPC ........... 514/517; 514/518; 514/532; 514/568; 514/570

(58) Field of Classification Search .................. 514/517, 514/518, 532, 568, 570
See application file for complete search history.

(56) References Cited

U.S. PATENT DOCUMENTS

| 3,954,767 | A | | 5/1976 | Esteve-Subirana |
|---|---|---|---|---|
| 4,115,648 | A | | 9/1978 | Esteve-Subirana |
| 4,837,378 | A | | 6/1989 | Borgman |
| 4,970,202 | A | | 11/1990 | Trigger |
| 5,374,772 | A | | 12/1994 | Carson et al. |
| 5,519,018 | A | | 5/1996 | Matusch et al. |
| 5,565,286 | A | * | 10/1996 | Lin .................. 430/5 |
| 5,656,286 | A | | 8/1997 | Miranda et al. |
| 5,698,595 | A | | 12/1997 | Boelle et al. |
| 6,281,203 | B1 | | 8/2001 | Touzan et al. |
| 6,664,406 | B1 | | 12/2003 | Coupland et al. |
| 6,787,573 | B2 | | 9/2004 | Nottet |
| 2002/0143052 | A1 | | 10/2002 | Lan-Hargest et al. |
| 2003/0216418 | A1 | | 11/2003 | Stogniew et al. |
| 2004/0167222 | A1 | | 8/2004 | Brooks et al. |
| 2005/0175559 | A1 | | 8/2005 | DiNardo et al. |
| 2006/0258730 | A1 | | 11/2006 | Allegretti et al. |
| 2007/0032471 | A1 | | 2/2007 | Torrens Jover et al. |
| 2007/0149618 | A1 | | 6/2007 | Cuevas Sanchez et al. |
| 2008/0113947 | A1 | | 5/2008 | Cuevas Sanchez et al. |
| 2008/0113948 | A1 | | 5/2008 | Cuevas Sanchez et al. |
| 2008/0114060 | A1 | | 5/2008 | Cuevas Sanchez et al. |
| 2008/0114063 | A1 | | 5/2008 | Sanchez et al. |
| 2008/0114075 | A1 | | 5/2008 | Cuevas Sanchez et al. |
| 2008/0125485 | A1 | | 5/2008 | Cuevas Sanchez et al. |
| 2008/0125486 | A1 | | 5/2008 | Sanchez et al. |
| 2009/0111779 | A1 | | 4/2009 | Cuevas Sanchez et al. |

FOREIGN PATENT DOCUMENTS

| EP | 0204987 | 5/1986 |
|---|---|---|
| EP | 1719509 | 11/2006 |
| JP | 8283152 | 10/1996 |
| WO | WO-96/17589 | 6/1996 |
| WO | WO-96/25159 | 8/1996 |
| WO | WO-2005/013962 | 2/2005 |
| WO | WO-2005/023305 | 3/2005 |
| WO | WO-2005/077352 | 8/2005 |
| WO | WO-2006/029484 | 3/2006 |
| WO | WO-2006/069806 | 7/2006 |

OTHER PUBLICATIONS

Remington's Pharmaceutical Sciences, pp. 420-425, 1980.*
Anwar et al. The development of actinic keratosis into invasive squamous cell carcinoma: evidence and evolving classification schemes. Clinics in Dermatology, 22: 189-196, 2004.*
Cuevas et al. Case Letters: Treatment of basal cell carcinoma with dobesilate. J. Am. Acad. Dermatol. Sep. 2005, vol. 53, No. 3.*
Stockfleth et al. Successful treatment of actinic keratosis with imiquimod cream 5%: a report of six cases. British Journal of Dermatology, 2001, 144: 1050-1053.*
Peck. Topical tretinoin in actinic keratosis and basal cell caricnoma. Journal of the American Academy of Dermatology, vol. 15, Issue 4, Part 2, Oct. 1986, pp. 829-835.*
"Actinic Keratosis and Other Precancers", http//www.skincancer.org 2008, 3 pgs.
"Causes of Barrett's Esophagus", http://digestive-system.emedtv.com/barrett's-esophagus/causes-of-barrett's-esophagus.html Nov. 2006, 3 pgs.
"Crohn's Disease", http://cholitis.emedtv.com/crohn'sdisease/crohn's-disease-causes.html 2008, 3 pgs.
"Definition of Rosacea", *American Heritage Medical Dictionary*, www.freedictionary.com 2007, 6 pgs.
"Psoriasis—Basics Facts—What Is Psoriasis", http://www.psoriasisguide.com/usus_basics/what_is_psoriasis.html 2 pgs., 2005.
"Remington's Pharmaceutical Sciences", 1980, 7 pgs.

(Continued)

*Primary Examiner* — Anna Pagonakis
(74) *Attorney, Agent, or Firm* — Servilla Whitney LLC; Kenneth M. Zeidner

(57) ABSTRACT

The present invention relates to the use of a 2,5-dihydroxybenzene derivative represented by Formula (I) or a pharmaceutically acceptable salt, solvate, isomer, or prodrug thereof for the therapeutic and/or prophylactic treatment of, inter alia, actinic keratosis.

20 Claims, 22 Drawing Sheets

OTHER PUBLICATIONS

"What is Rosacea?". http://www.rosacea.net/, 2005, 1 pg.

Adank, Christian et al., "Calcium Dobesilate in Diabetic Retinopathy", *Ophthalmologica*, Basel 190 1985, 102-111.

Angulo, Javier et al., "Calcium dobesilate potentiates endothelium-derived hyperpolarizing factor-mediated relaxation of human penile resistance arteries", *British Journal of Pharmacology 000* 2003, 1-9.

Anwar, Jamshaid et al., "The Development of Actinic Keratosis into Invesive Squamous Cell Cardinoma: Evidence and Evolving Classification Schemes", *Clinics in Dermatology 22* 2004, 189-196.

Arhanic, V. et al., "Attempts at Treating Bureosis with Angioprotective Agents", *Annals of the Dr. M. Stojanovic Hospital*, vol. 15:120 1976, 9 pgs.

Benakis, A. et al., "Localisation, distribution, eliination et metabolisme du dihydroxy-2,5, benzene sulfonate de Ca (Dobesilate de Ca) marque par le S35 chez la souris, le rat et le lapin", *Congres International de Therapeutique* 1974, 16 pgs.

Benarroch, Isaac S. et al., "Treatment of Blook Hyperviscosity with Calcium Dobesilate in Patients with Diabetic Retinopathy", *Ophthalmic Res. 17* 1985, 131-138.

Berthet, P. et al., "Calcium Dobesilate: Pharmacological Profile Related to its Use in Diabetic Retinopathy", *IJCP.*, vol. 53, No. 8 Dec. 1999, 631-636.

Bhushan, M. et al., "Recent advances in cutaneous angiogenesis", *British Journal of Dermatology 147* 2002, 418-425.

Brannon, Md, Heather, "Atopic Dermatitis Treatment", http://dermatology.about.com/cs/eczemadermatitis/a/stopictx.htm Dec. 23, 2005, 2 pgs.

Brunet, J. et al., "In vitro antioxidant properties of calcium dobesilate", *Fundam Clin Pharmacol 12* 1998, 205-212.

Catalogo de especialidades farmaceuticas 1991, *Consejo General De Colegios Oficiales De Farmaceuticos* 1991, 4 pgs.

Cuevas, P. et al., "Therapeutic Response of Rosacea to Dobesilate", *Eur. J. Med. Res.*, vol. 10 2005, pp. 454-456.

Cuevas, P. et al., "Treatment of basal cell carcinoma with dobesilate", *Am Acad Dermatol* 2005, 526-527.

Cuevas, P., et al., "Topical Treatment of Actinic Keratoses with Potassium Dobesilate 5% Cream. A Preliminary Open-Label Study", *Eur J. Med Res 16*, 2011, 67-70.

Cuevas, Pedro et al., "Dobesilate in the Treatment of Plaque Psoriasis", *Eur J Med Res 10* 2005, 373-376.

Divers, A.K. et al., "Keratoacanthoma centrifugum marginatum: a diagnostic and therapeutic challenge", *Curtis*, vol. 73, No. 4 2004, 257-262.

Dormond, Olivier et al., "Inhibitor of tumor angiogenesis by non-steroidal anti-inflammatory drugs: emerging mechanisms and therapeutic perspectives", *Drug Resistance Updates 4* 2002, 314-321.

Dorwald, F. Z., "Side Reactions in Organic Synthesis. A Guide to Sucessful Synthesis Design", *Wiley-VCH Verlag GmbH & Co.* 2005, 4 pgs.

English translation of Acnisdin and Acnisdin Retinoico entries in Catalogo de especialidades farmaceuticas, *Consejo General de Colegios Oficiales De Farmaceuticos* 1991, 2 pgs.

Final Office Action in U.S. Appl. No. 12/257,854, dated Mar. 1, 2012, 9 pgs.

Gambichler, T. et al., "Cytokine mRNA expression in basal cell carcinoma", *Arch Dermatol Res 298* 2006, 139-141.

Glioma Brain Tumors, http://www.sfn.org/index.aspx?pagename=brainbriefings_gliomabraintumors 2008, 2 pgs.

Goldman, Lee et al., "Principles of Cancer Therapy", *Cecil Textbook of Medicine*, vol. 1, W.B. Saunders Company 2000, 1060-1074.

Graber, R. et al., "Calcium Dobesilate protects human peripheral blood mononuclear cells from oxidation and apoptosis", *Apoptosis 3* 1998, 41-49.

Hodge, David R. et al., "The role of IL-6 and STAT3 in inflammation and cancer", *European Journal of Cancer 41* 2005, 2502-2512.

Hornick, Jason L. et al., "A New Chemically Modified Chimeric TNT-3 Monoclonal Antibody Directed Against DNA for the Radioimmunotherapy of Solid Tumors", *Cancer Biotherapy & Radiopharmaceuticals*, vol. 13, No. 4 1998, 255-268.

International Search Report of PCT/EP/2007/058440, mailed on Feb. 22, 2008, 5 pages.

International Search Report of PCT/EP2007/058438, mailed on Nov. 27, 2007, 4 pages.

International Search Report of PCT/EP2007/058439, mailed on Nov. 28, 2007, 4 pages.

International Search Report of PCT/EP2007/058440, mailed on Feb. 22, 2008, 5 pages.

International Search Report of PCT/EP2007/058441, mailed on Nov. 14, 2007, 4 pages.

International Search Report of PCT/EP2007/058443, mailed on Nov. 9, 2007, 3 pages.

International Search Report of PCT/EP2007/058444, mailed on Nov. 28, 2007, 4 pages.

International Search Report of PCT/EP2007/058445, mailed on Nov. 26, 2007, 4 pages.

International Search Report of PCT/EP2007/058446, mailed on Nov. 30, 2007, 4 pages.

International Search Report of PCT/EP2007/058447, mailed on Dec. 3, 2007, 4 pages.

International Search Report of PCT/EP2007/058451, mailed on Nov. 30, 2007, 4 pages.

International Search Report of PCT/EP2007/058453, mailed on Jul. 15, 2008, 6 pages.

International Search Report of PCT/EP2007/058454, mailed on Feb. 19, 2008, 4 pages.

International Search Report of PCT/EP2007/058456, mailed on Dec. 6, 2007, 7 pages.

International Search Report of PCT/ES2005/070017, mailed on Jun. 22, 2005, 2 pages.

Jee, S. H. et al., "The Phosphotidyl Inositol 3-Kinase/Akt Signal Pathway is Involved in Interleukin-6-mediated Mcl-1 Upregulation and Anti-apoptosis Activity in Vasal Cell Carcinoma Cells", *The Journal of Investigative Dermatology*, vol. 119, No. 5 2002, 1121-1127.

Jee, Shiou-Hwa et al., "Interleukin-6 Induced Basic Fibroblast Growth Factor-Dependent Angiogenesis in Basal Cell Carcinoma Cell Line via JAK/STAT3 and PI3-Kinase/Akt Pathways", *J Invest Dermatology 123* 2004, 1169-1175.

Jee, Shiou-Hwa et al., "Overexpression of interleukin-6 in human basal cell carcinoma cell lines increases anti-apoptotic activity and tumorigenic potency", *Onogena 20* 2001, 198-208.

Jegasothy, Brian V. et al., "Tacrolimus (FK 506)—A New Therapeutic Agent for Severe Recalcitrant Psoriasis", *Arch Dermatol*, vol. 128 Jun. 1992, 781-785.

Johnson, JL et al., "Relationships between drug activity in NCI preclinical in vitro and in vivo models and early clinical trials", *British Journal of Cancer 94*(10) 2001, 1424-1431.

Jordan, V. C., "Tamoxifen: A Most Unlikely Pioneering Medicine", *Nature Reviews Drug Discovery*, vol. 2 2003, 205-213.

Karasek, Marvin A., "Progress in our understanding of the biology of psoriasis", *Cutis*, vol. 64, Iss. 5 Nov. 1999, 5 pgs.

Kaur, Charandeep et al., "An open trial of calcium dobesilate in patients with venous ulcers and stasis dermatitis", *International Journal of Dermatology 42* 2003, 147-152.

Khawli, Leslie A. et al., "Comparison of Recombinant Derivatives of Chimeric TNT-3 Antibody for the Radioimaging of Solid Tumors", *Hybridoma and Hybridomics*, vol. 22, No. 1 2003, 1-10.

Kocak, Md, Mukadder et al., "Examination of Bcl-2, Bcl-X and bax protein expression in psoriasis", *International Journal of Dermatology 42* 2003, 789-793.

Lameynardie, Stephane et al., "Inhibition of choroidal angiogenesis by calcium dobesilate in normal Wistar and disbetic GK rats", *European Journal of Pharmacology 510* 2005, 149-156.

Lens, M. et al., "Current clinical overview of cutaneous melanoma", *British Journal of Nursing*, vol. 17, No. 5 2008, 2 pgs.

Losa, Gabriele A. et al., "Preventionof Oxidation and Apoptosis in Human Peripheral Blood Mononuclear Cells Exposed to Caldium Dobesilate", *International Journal of Angiology 8* 1999, 511-515.

Lozano, Rosa M. et al., "Solution Structure of Acidic Fibroblast Growth Factor Bound to 1,3,6-Naphthalenetrisulfonate: A Minimal Model for the Anti-tumoral Actionof Suramins and Suradistas", *J. Mol. Biol. 281* 1998, 899-015.

Michal, M. et al., "Effect of Calcium Dobesilate on Platelet Function", *Thrombosis Research 51* 1988, 593-605.

Newell, B. et al., "Comparison of the microvasculature of basal cell carcinoma and actinic keratosis using intravital microscopy and immunohistochemistry", *British Journal of Dermatology 149* 2003, 105-110.

Niwa, Y. et al., "Topical applicationof the immunosuppressant tacrolimus accelerates carcinogenesis in mouse skin", *British Journal of Dermatology 149* 2003, 960-067.

Nour, A. F. et al., "Preliminary Clinical Study with Calcium Dobesilate in Fibrocystic Disease of the Breast", *Acta Therapeutica*, vol. 12. No. 3 1986, 233-241.

O'Grady, Anthony et al., "COX-2 Expression Correlates With Microvessel Density in Non-Melanoma Skin Cancer From Renal Transplant Recipients and Immunocompetent Individuals", *Human Pathology*, vol. 35, No. 12 2004, 1549-1555.

Oh, Chang-Keun et al., "Expression of Basic Fibroblast Growth Factor, Vascular Endothelial Growth Factor, and Thrombospondin-1 Related to Microvessel Density in Nonaggressive and Aggressive Basal Cell Carcinomas", *The Journal of Dermatology*, Vo. 30 2003, 306-313.

PCT IPRP in PCT/EP2007/058438, dated Nov. 21, 2008, 8 pgs.

PCT IPRP in PCT/EP2007/058439, dated Dec. 1, 2008, 6 pgs.

Pelle, Michelle T. et al., "Rosacea: II. Therapy", *J Am Acad Dematol*, vol. 51 2004, pp. 499-512.

Reply to Written Opinion in PCT/EP2007/058440, dated Jul. 17, 2008, 30 pgs.

Ruiz, Emilio et al., "Calcium Dobesilate Increases Endothelium-Dependent Relaxation in Endothelium-Injured Rabbit Aorta", *Pharmacological Research*, vol. 38, No. 5 1998, 361-366.

Rutkowski, Suzanne, "Mystified by Your Medications?", *Asthma Magazine* 2001, 9-12.

Sausville, Edward A. et al., "Contributions of Human Tumor Xenografts to Anticancer Drug Development", *Cancer Res 66*(7) Apr. 1, 2006, 3351-3354.

Schon, Md, Michael et al., "Psoriasis", *The New England Journal of Medicine* 2005, 1899-1912.

Schulze, H. J. et al., "Imiquimod 5% cream for the treatment of superficial basal cell carcinoma: results from a randomized vehicle-controlled phase III study in Europe", *British Journal of Dermatology 152* 2005, 939-947.

Sintov, Amnon C. et al., "Percutaneous penetration and skin metabolism of ethylsalicylate-containing agent, UT-2100: in-vitro and in-vivo evaluation in guinea pigs", *Journal of Controlled Release 79* 2002, 113-122.

Skov, L. et al., "Basal cell carcinoma is associated with high TNF-a release but not with TNF-a polymorphism at position 308", *Experimental Dermatology 12* 2003, 772-776.

Staibano, Md, S. et al., "The Prognostic Significance of Tumor Angiogenesis in Nonaggressive and Aggressive Basal Cell Carcinoma of the Human Skin", *Human Pathology*, vol. 27 No. 7 1996, 695-700.

Stanton, Anthony W. et al., "Expansion of Micorvascular Bed and Increased Solute Flux in Human Basal Cell Carcinoma in Vivo, Measured by Fluorescein Video Angiography", *Cancer Research 63* 2003, 3969-3979.

Stanwell, Caroline et al., "The Erbstatin Analogue Methyl 2,5-Dihydroxycinnamate Cross-Links Proteins and is Cytotoxic to Normal and Neoplastic Epithelial Cells by a Mechanism Independent of Tyrosine Kinase Inhibition", *Cancer Research*, vol. 55 1995, 4950-4956.

Stockfleth, E. et al., "Successful treatment of actinic keratosis with imiquimod cream 5%: a report of six cases", *British Journal of Dermatology, 144* 2001, 1050-1053.

Suschek, Christoph et al., "Dobesilate enhances endothelial nitric oxide synthase-activity in macro- and microvascular endothelial cells", *British Journal of Pharmacology 122* 1997, 1502-15-8.

Takatsuka, Yoshikazu et al., "Various Analogues to Anthranilic Acid and Their Anti-Cancer Effects", *Mie Medical Journal*, vol. XVII, No. 1 1987, 11 pgs.

Tejerina, T. et al., "Calcium Dobesilate: Pharmacology and Future Approaches", *Gen. Pharmac.*, vol. 31, No. 3 1998, 357-360.

Tjiu, Jeng-Wei et al., "Cyclooxygenase-2 Overexpression in Human Basal Cell Carcinoma Cell Line Increases Antiapoptosis, Angiogenesis, and Tumorigenesis", *The Society for Investigative Dermatology* 2006, 1143-1151.

Tjiu, Jeng-Wei et al., "Tumor-Associated macrophage-Induced Invasion and Angiogenesis of Human Basal Cell Carcinoma Cells by Cyclooxygenase-2 Induction", *Journal of Investigative Dermatology* 2009, 1016-1025.

Travis, Lisa et al., "Mdical Backgrounder: Psoriasis", *Drugs of Today, 38* (12) 2002, 847-865.

Trozak, Daniel J., "Topical corticosteriod therapy in psoriasis vulgaris: Update and new strategies", *Cutis.*, vol. 64, Iss. 5 5 pgs., Nov. 1999.

Vippagunta, Sudha R. et al., "Crystalline solids", *Advanced Drug Delivery Reviews 48* 2001, 3-26.

Wilkin, Jonathan et al., "Standard classification of rosacea: Report of the National Rosacea Society Expert Committee on the Classification and Staging of Rosacea", *Acad. Derato. 46:L* 2002, 584-587.

Wolf, Manfred E. , "Burger's medicinal Chemistry and Drug Discovery", Fifth Edition vol. 1: *Principles and Practice* 1995, 4 pgs.

Wollina, U. et al., "Toxicity of Methotrexate Treatment in Psoriasis and Psoriatic Arthritis—Short and Long-Germ Toxicity in 104 Patients", *Clin Rheumatol 20* 2001, 406-410.

Written Opinion of PCT/EP2007/058438, mailed on Nov. 27, 2007, 7 pages.

Written Opinion of PCT/EP2007/058440, mailed on Feb. 22, 2008, 8 pages.

Written Opinion of PCT/ES2005/070017, mailed on Jun. 22, 2005, 3 pages.

Yamada, Katsuhisa et al., "Inhibitory Effect of Diacetyl Gentisic Acid on Melanogenesis", *Journal of Japanese Cosmetic Science Society*, vol. 22, No. 3 1998, 169-174.

\* cited by examiner

USE OF 2,5-DIHYDROXYBENZENE DERIVATIVES FOR TREATING ACTINIC KERATOSIS

RELATED APPLICATIONS

This application is a continuation-in-part of U.S. Ser. No. 11/506,469, which is a national stage filing under 35 U.S.C. §371 of International Application Number PCT/ES05/70017, filed Feb. 16, 2005, which claims the benefit of priority under 35 U.S.C. §119 of ES Application Number P200400371, filed Feb. 17, 2004. In addition, this application claims the benefit of priority under 35 U.S.C. §119 of ES Application No. P200602219, filed Aug. 16, 2006 and of ES Application No. P200701857, filed Jul. 2, 2007. The foregoing applications, and all documents cited therein, are hereby incorporated herein by reference in their entirety.

FIELD OF THE INVENTION

The present invention relates to the use of 2,5-dihydroxybenzene derivatives to manufacture medicaments useful to prevent and/or treat skin aging due to exposure to ultraviolet B rays (UVB), or to exposure to sun rays in general, to treat pathologies associated to said skin photoaging such as skin wrinkles or actinic keratosis, pigmentation and hyperpigmentation of the skin, as well as to treat obesity due to excessive adipogenesis, hirsutism, hypertricosis and viral warts.

BACKGROUND OF THE INVENTION

Chronic exposure to ultraviolet B rays (UVB: 290-320 nm wavelength), or solar rays, in general (comprising, among other wavelengths, that of UVB radiation) produces skin aging (photoaging) due to the accumulation of DNA damage and on the structural proteins of the skin, evidencing in the form of fine wrinkles, laxity with loss of skin elasticity, elastosis, yellowish staining with localized areas of melanin hyperpigmentation (solar, actinic or senile lentigo). Besides, skin photoaging is associated with the appearance of comedoes that are more evident in the "cutis romboidalis" at the rear part of the neck. In the histological test, an epidermic atrophy and degenerative changes in elastic fibers of the dermis may be observed (Pearse A D, Gaskell S A, Marks R. J Invest Dermatol 1987; 88 83-87; Berton T R, Mitchell D L, Fischer S M, Looniskar M F. J Invest Dermatol 1997; 109: 340-347). Furthermore, chronic exposure to UVB rays is a risk factor for the appearance of benign lesions, such as seborrheic keratosis, and premalignant lesions such as actinic keratosis (Kripke M L. Cancer Res 1994; 54: 6102-6105). Currently, there is no effective treatment for skin photoaging (Dermatol Surg. Special Issue: Cosmeceuticals. Invited editors: Draelos Z D, Brody H J. 2005).

On the other hand, the hair follicle is the functional unit for hair elongation. Hirsutism is a clinical condition in which there in an excessive hair growth with an androgenic-type pattern (face, thorax, areolas, linea alba, lower part of the back, buttocks, limbs and external genitals) produced by an increase in the androgenic activity. Hypertricosis is a condition in which there is an excessive hair growth in areas sensitive and non-sensitive to androgens.

Obesity is a disease produced when the energy intake exceeds and produces an excess of adipose tissue. This process is regulated by the control on the intake, on the energy expenditure and efficiency and on the adipogenesis). (Gregoire F M. *Exp Biol Med*, 2001, 226: 997-1002; Palou A et al. *Eur J Nutr,* 2000, 39: 127-144). Prevention and/or treatment of obesity is a very important factor to reduce morbidity and mortality rates associated to cardiovascular disorders and to type 2 diabetes, which represent a high health and social cost in industrialized countries. Currently, there is no effective treatment for obesity. The effective therapies to treat obesity should interfere with the development of adipose tissue. To increase the adipose tissue mass, it is essential that preadipocytes are differentiated in a mature adipocyte phenotype. Besides morphological changes, the differentiation process of preadipocyte into adipocyte is accompanied by metabolic processes such as the capacity of storing energy in the form of triglycerides (McDougald O A, Lane M D. *Annu Rev Biochem,* 1995, 345-373; Spiegelman B M, Flier J S. *Cell* 1996, 87: 377-389). Therefore, the pharmacological inhibition of the differentiation of preadipocytes into adipocytes represents a therapeutic strategy to treat obesity.

There is a need to find alternative treatments to the current ones for skin photoaging, hirsutism, or obesity; both from the aesthetic and therapeutic points of view, based on the use of active principles.

SUMMARY OF THE INVENTION

Surprisingly, the inventors have found that 2,5-dihydroxybenzene derivatives, the pharmaceutically acceptable salts and solvates thereof, as well as isomers and prodrugs thereof are useful to prevent and/or therapeutically treat skin aging due to exposure to ultraviolet rays B (UVB), or to exposure to sun rays in general, to treat pathologies associated with said skin photoaging such as skin wrinkles, actinic keratosis, skin pigmentation and hyperpigmentation, as well to treat hirsutism and hypertricosis, obesity due to excessive adipogenesis, and to treat viral warts.

In certain embodiments, the invention provides a method for the treatment and/or prophylaxis of actinic keratosis, comprising administering to a subject in need thereof, an effective amount of a 2,5-dihydroxybenzene derivative represented by Formula (I) or a pharmaceutically acceptable salt, solvate, isomer, or prodrug thereof, wherein the compound of Formula (I) is:

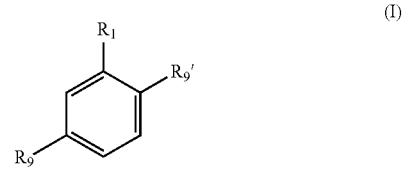

wherein:

$R_1$ is —$(CH_2)_a$Y or —CH=CH—$(CH_2)_p$Y;

Y is —$SO_3H$, —$SO_3^-.X^+$, —$SO_3R_3$, —$PO_3H$, —$PO_3^-.X^+$, —$PO_3R_3$, —$CO_2H$, —$CO_2^-.X^+$ or —$CO_2R_3$;

$X^+$ is an organic cation or an inorganic cation, such that the general charge of the compound of Formula (I) is neutral;

$R_9$ and $R_{9'}$ are independently selected from —OH and —$OR_2$, wherein when $R_9$ and $R_{9'}$ are both —$OR_2$, then said $R_9$ and $R_{9'}$ can be the same or different;

$R_2$ is a substituted or unsubstituted alkyl group, a substituted or unsubstituted aryl group, a substituted or unsubstituted alkylsulfonyl group, a substituted or unsubstituted arylsulfonyl group, a substituted or unsubstituted alkylcarbonyl group or a substituted or unsubstituted arylcarbonyl group;

R₃ is a substituted or unsubstituted alkyl group or a substituted or unsubstituted aryl group;

a is a number selected from 0, 1, 2, 3, 4, 5 and 6; and p is a number selected from 0, 1, 2, 3, 4, 5 and 6.

In certain embodiments, Y is selected from —SO₃H, —SO₃⁻.X⁺, —SO₃R₃, —CO₂H, —CO₂⁻.X⁺ and —CO₂R₃. In other embodiments, at least one of R₉ and R₉, are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group. In yet other embodiments, R₂ is selected from methylcarbonyl, phenylsulfonyl, 4-methylphenylsulfonyl, benzylsulfonyl, benzyl and phenyl.

In certain embodiments, the compound of Formula (I) is selected from the group consisting of: 2,5-dihydroxybenzenesulfonic acid (Dobesilate), 5-hydroxy-2-{[(4-methylphenyl)sulfonyl]oxy}benzenesulfonic acid; 2-hydroxy-5-{[(4-methylphenyl)sulfonyl]oxy}benzenesulfonic acid; 2,5-bis{[(4-methylphenyl)sulfonyl]oxy}benzenesulfonic acid; 2-(acetyloxy)-5-hydroxybenzenesulfonic acid; 5-(acetyloxy)-2-hydroxybenzenesulfonic acid; 2,5-bis(acetyloxy)benzenesulfonic acid; 2-(benzyloxy)-5-hydroxybenzenesulfonic acid; 5-(benzyloxy)-2-hydroxybenzenesulfonic acid; 2,5-bis(benzyloxy)benzenesulfonic acid; 2,5-dihydroxybenzene homosulfonic acid (homodobesilate); 5-hydroxy-2-{[(4-methylphenyl)sulfonyl]oxy}benzenehomosulfonic acid; 2-hydroxy-5-{[(4-methylphenyl)sulfonyl]oxy}benzenehomosulfonic acid; 2,5-bis{[(4-methylphenyl)sulfonyl]oxy}benzenehomosulfonic acid; 2-(acetyloxy)-5-hydroxybenzenehomosulfonic acid; 5-(acetyloxy)-2-hydroxybenzenehomosulfonic acid; 2,5-bis(acetyloxy)benzenehomosulfonic acid; 2-(benzyloxy)-5-hydroxybenzenehomosulfonic acid; 5-(benzyloxy)-2-hydroxybenzenehomosulfonic acid; 2,5-bis(benzyloxy)benzenehomosulfonic acid; 2,5-dihydroxybenzoic acid (gentisic acid), 5-hydroxy-2-{[(4-methylphenyl)sulfonyl]oxy}benzoic acid; 2-hydroxy-5-{[(4-methylphenyl)sulfonyl]oxy}benzoic acid; 2,5-bis{[(4-methylphenyl)sulfonyl]oxy}benzoic acid; 2-(acetyloxy)-5-hydroxybenzoic acid; 5-(acetyloxy)-2-hydroxybenzoic acid; 2,5-bis(acetyloxy)benzoic acid; 2-(benzyloxy)-5-hydroxybenzoic acid; 5-(benzyloxy)-2-hydroxybenzoic acid; 2,5-bis(benzyloxy)benzoic acid; 2,5-dihydroxyhomobenzoic acid (homogentisic acid); 5-hydroxy-2-{[(4-methylphenyl)sulfonyl]oxy}homobenzoic acid; 2-hydroxy-5-{[(4-methylphenyl)sulfonyl]oxy}homobenzoic acid; 2,5-bis{[(4-methylphenyl)sulfonyl]oxy}homobenzoic acid; 2-(acetyloxy)-5-hydroxyhomobenzoic acid; 5-(acetyloxy)-2-hydroxyhomobenzoic acid; 2,5-bis(acetyloxy)homobenzoic acid; 2-(benzyloxy)-5-hydroxyhomobenzoic acid; 5-(benzyloxy)-2-hydroxyhomobenzoic acid; 2,5-bis(benzyloxy)homobenzoic acid; 3-(2,5-dihydroxyphenyl)-2-propenoic acid (2,5-dihydroxycinnamic acid); 3-(5-hydroxy-2-{[(4-methylphenyl)sulfonyl]oxy}phenyl)-2-propenoic acid; 3-(2-hydroxy-5-{[(4-methylphenyl)sulfonyl]oxy}phenyl)-2-propenoic acid; 3-(2,5-bis{[(4-methylphenyl)sulfonyl]oxy}phenyl)-2-propenoic acid; 3-(2-(acetyloxy)-5-hydroxyphenyl)-2-propenoic acid; 3-(5-(acetyloxy)-2-hydroxyphenyl)-2-propenoic acid; 3-(2,5-bis(acetyloxy)phenyl)-2-propenoic acid; 3-(2-(benzyloxy)-5-hydroxyphenyl)-2-propenoic acid; 3-(5-(benzyloxy)-2-hydroxyphenyl)-2-propenoic acid; 3-(2,5-bis(benzyloxy)phenyl)-2-propenoic acid; and pharmaceutically acceptable salts, solvates and prodrugs thereof.

In certain embodiments, the compound of Formula (I) comprises an ester at position 1.

In some embodiments, the compound of Formula (I) is selected from: 2-(acetyloxy)-5-hydroxybenzenesulfonic acid; 5-(acetyloxy)-2-hydroxybenzenesulfonic acid and 2,5-bis(acetyloxy)benzenesulfonic acid.

In yet other embodiments, the compound of Formula (I) is selected from the group consisting of: calcium 2,5-dihydroxybenzenesulfonate (calcium Dobesilate); potassium 2,5-dihydroxybenzenesulfonate (potassium Dobesilate); magnesium 2,5-dihydroxybenzenesulfonate (magnesium Dobesilate); diethylamine 2,5-dihydroxybenzenesulfonate (Ethamsylate);

In a particular embodiment, the compound of Formula (I) is calcium 2,5-dihydroxybenzenesulfonate (calcium Dobesilate).

In another embodiment, the compound of Formula (I) is potassium 2,5-dihydroxybenzenesulfonate (potassium Dobesilate).

In certain embodiments, the invention provides a method for the treatment or prophylaxis of actinic keratosis, wherein the actinic keratosis is selected from the group consisting of: hypertrophic, atrophic, bowenoid, and acantholythic keratosis.

Advantageously, a compound of Formula (I) is administered topically. In certain embodiments, the compound of Formula (I) is administered orally, buccally, transdermally, by inhalation, rectally, intravaginally, or otically.

In yet other embodiments, the invention provides a method for the treatment or prophylaxis of actinic keratosis further comprising administration of at least one additional therapeutic agent in addition to a compound of Formula (I).

Examples of suitable additional therapeutic agents include imiquimod, diclofenac, glycidic acid, trichloroacetic acid, colchicine, T4 endonuclease, 5-fluorouracil, isotretinoin, acitretin, cidofoir, 5-aminolevulinic acid, methyl aminolevulinate, hypericin, chemotherapeutic agent, a corticosteroid, an antibiotic, an analgesic, an immunomodulator, an immunosuppressant, an anti-angiogenic (including anti-VEGF, anti-FGF, anti-EGF and anti-HGF), a leukotriene modifier, an aminosalicylate, an anesthetic, a non-steroidal anti-inflammatory, a modifier of a solubilized interleukin receptor, a cytotoxic, an inhibitor of a tyrosine-kinase receptor, a protein kinase C inhibitor, and combinations of two or more thereof.

In certain embodiments, the invention provides a method for the treatment or prophylaxis of actinic keratosis comprising administration of a compound of Formula (I) and further comprising at least one coadjuvant therapy selected from the group consisting of: photodynamic therapy, cryotherapy, curettage, and surgery.

In certain embodiments, the invention provides for administration of a compound of Formula (I) for the treatment and/or prophylaxis of actinic keratosis, wherein the compound is administered at least once per week. In other embodiments, the compound is administered at least once per day or at least twice per day.

In certain embodiments, a compound of Formula (I) is present in a pharmaceutical composition in an amount of at least about 1% w/w. In other embodiments, the compound is present in a pharmaceutical composition in an amount of at least about 2.5 w/w, at least about 5% w/w, at least about 10% w/w, or at least about 15% w/w.

In yet other embodiments, a compound of Formula (I) is administered over a period of at least about one week. In certain embodiments, the compound is administered over a period of at least about four weeks.

These and other aspects of the present invention are described in detail herein.

DETAILED DESCRIPTION OF THE INVENTION

Figure 1:
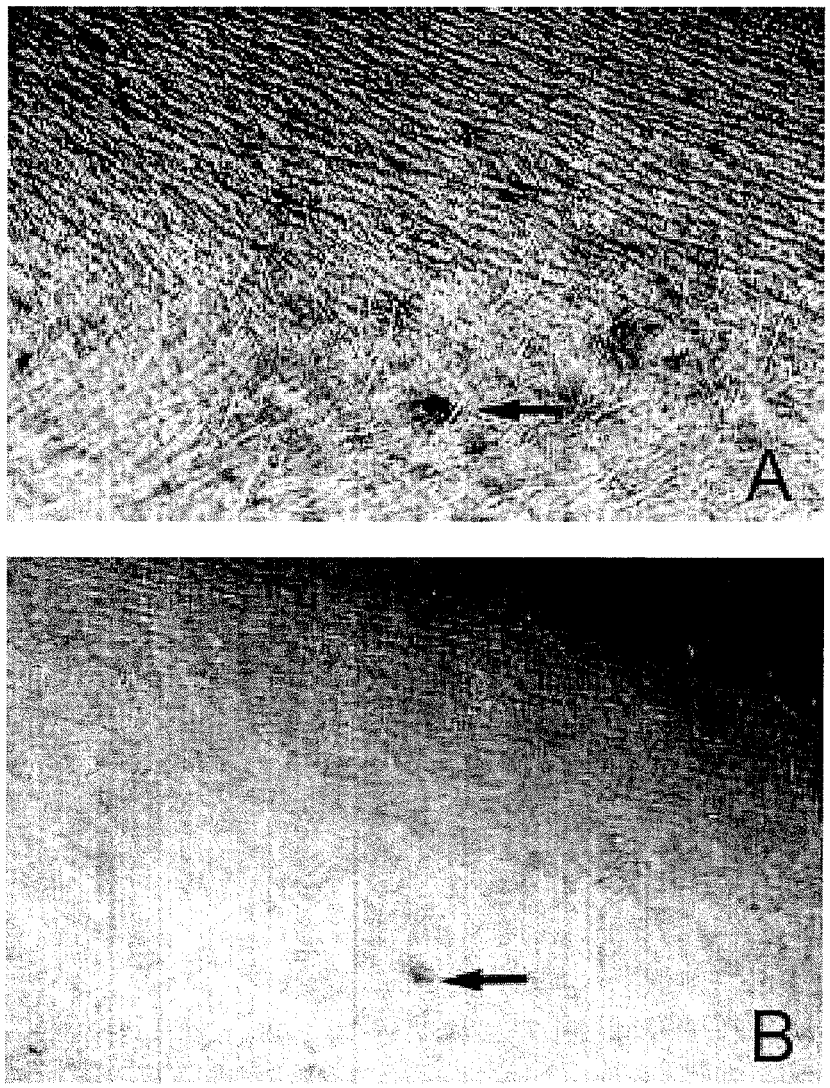
FIG. 1. Appearance of aged skin before treatment (A) and after topical treatment during three months with a cream containing 5% of 2,5-dihydroxybenzenesulfonic acid (B). The arrows indicate the same area of actinic lentigo before and after treatment.

The definitions of the terms and the chemical groups comprised in the formulas herein are as follows:

The term "patient" refers to animals, preferably mammals, and more preferably humans, and includes males and females, children and adults.

The expression "effective amount" refers to the amount of compound and/or composition effective to achieve the desired purpose.

The terms "treat" or "treatment" refer to the prophylactic use of compounds or compositions of the present invention to avoid the symptoms of the disease or condition, or the therapeutical use to improve an existing condition.

"Alkyl" refers to a linear or branched chain hydrocarbon radical comprising carbon atoms and hydrogen, with no unsaturations, with one to twelve, preferably one to eight, more preferably one to six carbon atoms, bound to the rest of the molecule by a single bond, for example, methyl, ethyl, n-propyl, i-propyl, n-butyl, t-butyl, n-pentyl, etc.

"Alkenyl" refers to a linear or branched chain hydrocarbon radical comprising carbon atoms and hydrogen atoms, containing at least one unsaturation, with two to twelve, preferably two to eight, more preferably two to six carbon atoms, bound to the rest of the molecule by a single bond.

"Cycloalkyl" refers to a saturated carbocyclic ring having between three and eight, preferably three to six carbon atoms. They may exhibit a bridged structure. Suitable cycloalkyl groups include, but are not limited to, cycloalkyl groups such as cyclopropyl, cyclobutyl, cyclopentyl or cyclohexyl.

"Alkynyl" refers to a linear or branched chain hydrocarbon radical comprising carbon atoms and hydrogen, containing at least one triple carbon-carbon bond, whether conjugated or not, with two to twelve, preferably two to eight, more preferably two to six carbon atoms, bound to the rest of the molecule by a single bond such as —CCH, —CH$_2$CCH, —CCCH$_3$, —CH$_2$CCCH$_3$.

"Aryl" refers to an aromatic hydrocabon radical containing from six to ten carbon atoms such as phenyl or naphthyl.

"Aralkyl" refers to an aryl group bound to the rest of the molecule by an alkyl group such as benzyl and phenetyl.

"Heterocycle" refers to a stable 3 to 15-membered ring comprised of carbon atoms and between one and five heteroatoms selected from the group consisting of nitrogen, oxygen and sulfur, preferably a 4 to 8-membered ring with two, three or four heteroatoms, more preferably a 5 or 6-membered ring with one, two or three heteroatoms. For the purpose of the present invention, the heterocycle may be a monocyclic, bicyclic or tryciclic ring system that may include fused ring systems; bridged structures; and the nitrogen, carbon or sulfur atoms in the heterocyclic radical may be optionally oxidized; the nitrogen atom may be optionally quaternized; and the heterocyclic radical may be partially or completely saturated or it may be aromatic. Examples of such heterocycles include, but are not limited to, azepines, benzimidazole, benzothiazole, furan, isothiazole, imidazole, indole, piperidine, piperazine, quinoline, thiadiazol, tetrahydrofuran.

Unless otherwise specified, the alkyl, cycloalkyl, alkenyl, alkynyl, aryl, aralkyl and heterocycle radicals may be optionally substituted by one, two or three substituents such as halo, alkyl, alkenyl, alkynyl, aryl, cycloalkyl, hydroxy, alkoxy, sulfoxy, O-Benzyl, O-Benzoyl, carboxyl, alkylcarboxyl, arylcarboxyl, alkylcarbonyl, arylcarbonyl, cyano, carbonyl, acyl, alkoxycarbonyl, amino, alkylamino, dialkylamino, arylamino, diarylamino, alkylarylamino, imino, alkylsulphinyl, amidyl, carbamoyl, sulfonamido, nitro, nitrite, nitrate, thionitrate and carboxamido.

The term "alkoxycarbonyl" refers to a compound having the formula —C(=O)O—, where the C-terminal is bound to the molecule and the O-terminal is bound to a carbon atom to form an ester function. Said carbon atom may be part of an alkyl, alkenyl, cycloalkyl, alkynyl, aryl, aralkyl or heterocyclic group.

The term "alkoxycarbonylalkyl" refers to a compound of the previously defined formula —C(=O)O—, wherein the C-terminal binds to a molecule through an alkyl group. The terms "aryloxy- arylalkoxy- or alkylaryloxy-carbonylalkyl" will be understood similarly to "alkoxycarbonylalkyl".

The term "arylalkyl" refers to an aryl radical, as defined herein, bound to an alkyl radical, as defined herein. The exemplary arylalkyl groups include benzyl, phenylethyl, 4-hydroxybenzyl, 3-fluorobenzyl, 2-fluorophenylethyl and the like.

The term "alkylaryl" refers to an alkyl group, as defined herein, to which an aryl group is bound, as defined herein. The exemplary alkylaryl groups include benzyl, phenylethyl, hydroxybenzyl, fluorobenzyl, fluorophenylethyl, and the like.

The term "alkylsulfonyl" refers to a $R_{50}$—$S(O)_2$—, wherein $R_{50}$ is a lower alkyl group, as defined herein.

The term "arylsulfonyl" refers to a $R_{55}$—$S(O)_2$—, wherein R55 is an aryl group, as defined herein.

The term "alkylsulphinyl" refers to a $R_{55}$—$S(O)_2$—, wherein R55 is an aryl group, as defined herein.

The term "arylsulphinyl" refers to a $R_{55}$—$S(O)_2$—, wherein $R_{55}$ is an aryl group, as defined herein.

The term "sulfonamide" refers to a —$S(O)_2$—$N(R_{51})(R_{57})$, wherein $R_{51}$ and $R_{57}$ are each independently a hydrogen atom, an alkyl group, an aryl group, heterocycle, as defined herein, or else $R_{51}$ and $R_{57}$ together form a heterocyclic ring, a cycloalkyl group or a bridged cycloalkyl group, as defined herein.

The term "alkylsulfonamide" refers to a sulfonamido group, as defined herein, bound to an alkyl group, as defined herein.

The term "arylsulfonamide" refers to a sulfonamido group, as defined herein, bound to an aryl group, as defined herein.

The term "alkylcarbonyl" refers to a $R_{52}$—$C(O)_2$—, wherein $R_{52}$ is an alkyl group, as defined herein.

The term "arylcarbonyl" refers to the $R_{55}$—$S(O)_2$— radical, wherein R55 is an aryl group, as defined herein.

The term "carboxamide" refers to a —$C(O)N(R_{52})(R_{58})$ radical, wherein $R_{52}$ and $R_{58}$ are each independently a hydrogen atom, an alkyl group, an aryl group or an heterocyclic group, as defined herein or else $R_{51}$ and $R_{57}$ together form an heterocyclic ring, a cycloalkyl group, or a bridged cycloalkyl group, as defined herein.

The term "carboxylic ester" refers to —$C(O)OR_{59}$, wherein $R_{59}$ is an alkyl group an aryl group or an heterocyclic group, as defined herein.

The term "alcoxyalkyl" refers to an alcoxy group, as defined herein, bound to an alkyl group, as defined herein. Examples of alcoxyalkyl groups are methoxymethyl, methoxyethyl, isopropoximethyl and the like.

The term "amine" refers to any organic compound containing at least one basic nitrogen atom.

The term "organic cation" refers to a positively charged organic ion. The exemplary organic cations include ammonium cations unsubstituted or substituted with alkyl, primary, secondary o tertiary amines, alkylamines, arylamines, cyclic amines, N,N'-dibenzylethylenediamine, and the like.

The term "inorganic cation" refers to a positively charged metal ion. The exemplary inorganic cations include Group I metal cations such as sodium, potassium, magnesium, calcium and the like.

The term "prodrug" refers to compounds that rapidly convert in vivo into pharmacologically active compounds. Prodrug design is generally studied in Hardma et al. (eds.), Goodman and Gilman's The Pharmacological Basis of Therapeutics, 9th ed., pages 11-16 (1996). A thorough study is presented in Higuchi et al., Prodrugs as Novel Delivery Systems, vol. 14, ASCD Symposium Series, and in Roche (ed.), Bioreversible Carriers in Drug Design, American Pharmaceutical Association and Pergamon Press (1987).

The compounds of the invention having one or more asymmetric carbon atoms may exist as optically pure enantiomers, pure diastereomers, mixtures of enantiomers, mixtures of diastereomers, racemic mixtures of enantiomers, diastereomeric racemates or mixtures of diastereomeric racemates. It should be clearly understood that the invention contemplates and includes these isomers and mixtures thereof within its scope.

The term "ester derivative of a compound of formula (I)" refers to the compound of formula (I) wherein at least one of $R_9$ and $R_{9'}$ is an ester group. For example, the ester derivative of 2,5-dihydroxybenzene sulfonic acid or dobesilate ester derivative refers to the compound 2,5-dihydroxybenzene sulfonic acid (dobesilate) wherein at least one of the hydroxyl groups has been esterified.

The term "ester of a compound of formula (I)" refers to an ester of the sulfonic or carboxylic acid group at position 1. For example, the ester of 2,5-dihydroxybenzensulfonic acid or ester of dobesilate refers to an ester of the sulfonic acid group at position 1.

The term "topical" refers to the administration of a compound by applying it on the body surface and includes, but is not limited to, transdermal administration and administration through the mucosa.

The term "transdermal" refers to the delivery of a compound that enters into the bloodstream through the skin.

The expression "through the mucosa" refers to the delivery of a compound that enters into the bloodstream through the mucous tissue.

The term "parenteral" refers to the administration of a compound by means of a subcutaneous, intravenous, intramuscular, intracardiac, intradermic, intraperitoneal, intrathecal or intrasternal injection; and also includes local or systemic infusion techniques.

The expression "penetration enhancement" or "permeation enhancement" refers to the increase in the permeability of the skin or mucous tissue to a pharmacologically active compound selected in such a way that it increases the penetration rate through the skin or mucous tissue.

"Excipients" or "vehicles" refers to the vehicle materials suitable for compound administration and include any such material known in the art such as, for example, any liquid, gel, solvent, liquid diluent, solubilizer, or the like, which is non-toxic and which does not show harmful interaction with any component of the composition.

The expression "sustained release" refers to the release of an active compound and/or composition such that the blood levels of the active compound are maintained within a desirable therapeutic range over a period of time. The sustained release formulation may be prepared using any conventional known method by a skilled in the art in order to obtain the desired release characteristics.

"Viral warts" refers to benign growths of the skin or mucosa.

"Actinic keratosis" refers to dry, squamous lesions with gritty texture formed in the external layer of the skin after years of exposure to ultraviolet light, such as solar rays.

"Seborrheic keratosis" refers to non-cancerous growth of the external layer of the skin.

"Obesity" refers to an excess accumulation of adipose tissue.

"Excessive adipogenesis" refers to an excess in the formation of adipose tissue.

"Hirsutism" refers to an excessive growth of hair in women in androgenic areas.

"Hypertricosis" is a general growth of body hair, not limited to certain areas.

"Skin photoaging" refers to an alteration in the skin caused by solar exposure.

"Skin wrinkles" refers to wrinkles produced on the skin due to cutaneous photoaging.

The term "therapeutic agent" includes any active agent that can be used to treat or prevent a disease described herein. "Therapeutic agents" include but are not limited to immunomodulatory treatments, such as a tacrolimus ointment or a pimecrolimus cream and the like; topical corticosteroids (cream, unguents, ointments or gels) or systemic corticosteroids; topical or systemic immunosupressants, such as, for example, cyclosporine, metrotrexate, azathioprine, and the like; phototherapy; emollients such as for example, white petrolatum, eucerin, urea cream, mineral oil, aluminum acetate, and the like; barrier creams, such as, for example, zinc oxide paste, and the like; moisturizing agents, such as, for example, menthol, camphor, and the like; local anesthetics, such as, for example, lidocaine, and the like; topical corticoids, such as, for example, triamcinolone acetate, and the like; systemic corticoids, such as, for example, prednisone, and the like; antihistamines, such as, for example, diphenhydramine, hydroxyzine, and the like; podophylline resin, locally applied; cantharin, only combined with podophylline; salicylic acid, locally applied; imiquimod; bleomycin; exfoliating agents, such as, for example, alpha hydroxy acids (glycolic acid, salicylic acid, lactic acid), trichloroacetic, phenols (carbolic acid, croton oil, and the like; diclofenac gel; 5-fluorouracyl, bleaching agents and photoprotectors, and the like. A therapeutic agent includes pharmaceutically acceptable salts thereof, prodrugs and pharmaceutical derivatives thereof.

In a first aspect, the present invention relates to the use of a compound of a 2,5-dihydroxybenzene represented by Formula (I) or a pharmaceutically acceptable salt or solvate, isomer or prodrug thereof to prepare a medicament for the cosmetic, therapeutic and/or prophylactic treatment of actinic keratosis, obesity due to excessive adipogenesis, hirsutism, hypertricosis, viral warts, pigmentation and/or hyperpigmentation of the skin wherein the compound of the Formula (I) is:

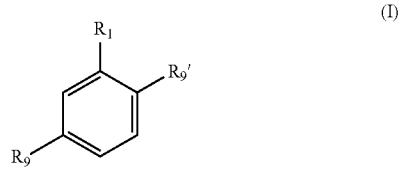

(I)

wherein:
R$_1$ is —(CH$_2$)$_a$Y or —CH=CH—(CH$_2$)$_p$Y;
Y is —SO$_3$H, —SO$_3$$^-$.X$^+$, —SO$_3$R$_3$, —PO$_3$H, —PO$_3$—.X$^+$, —PO$_3$R$_3$, —CO$_2$H, —CO$_2$$^-$.X$^+$ or —CO$_2$R$_3$;
X$^+$ is an organic cation or an inorganic cation, such that the general charge of the compound of Formula (I) is neutral;
R$_9$ and R$_{9'}$ are independently selected from —OH and —OR$_2$; wherein when R$_9$ and R$_{9'}$ are both —OR$_2$, then said R$_9$ and R$_{9'}$ can be the same or different;
R$_2$ is a substituted or unsubstituted alkyl group, a substituted or unsubstituted aryl group, a substituted or unsubstituted arylalkyl group, a substituted or unsubstituted alkylsulfonyl group, a substituted or unsubstituted arylsulfonyl group, a substituted or unsubstituted alkylarylsulfonyl group, a substituted or unsubstituted arylalkysulfonyl group, a substituted or unsubstituted aryloxyalkyl group, a substituted or unsubstituted alkylcarbonyl group or an arylcarbonyl group, a carboxyl group, a substituted or unsubstituted alkoxycarbonyl group, a substituted or unsubstituted carboxyalkyl group, in particular —CH$_2$—COOH, or a substituted or unsubstituted alkoxy- aryloxy- arylalkoxy- or alkylaryloxy-carbonylalkyl, in particular —CH$_2$—COOR$_3$;
R$_3$ is a substituted or unsubstituted alkyl group, a substituted or unsubstituted aryl group, a substituted or unsubstituted arylalkyl group, or a substituted or unsubstituted alkylaryl group;
a is number selected from 0, 1, 2, 3, 4, 5 and 6; and
p is number selected from 0, 1, 2, 3, 4, 5 and 6.

In a particular embodiment, the 2,5-dihydroxybenzene derivatives of the invention or any of the pharmaceutically acceptable salts thereof are those that are represented by Formula (I) comprising Dobesilate, Homodobesilate, dobesilate esters derivatives and the pharmaceutically acceptable salts thereof for the treatment of actinic keratosis, obesity due to excessive adipogenesis, hirsutism, hypertricosis and viral warts.

Particularly, the present invention comprises 2,5-dihydroxybenzene derivatives of the invention or any of the pharmaceutically acceptable salts thereof, represented by Formula (I) comprising gentisic acid, homogentisic acid, gentisic acid ester derivatives, homogentisic acid ester derivatives, 2,5-dihydroxycinnamic acid, 2,5-dihydroxycinnamic acid ester derivatives, homodobesilate ester derivatives, and the pharmaceutically acceptable salts thereof, for the treatment of actinic keratosis, obesity due excessive adipogenesis, hirsutism, hypertricosis and viral warts.

In a particular embodiment of the invention 2,5-dihydroxybenzenic derivatives of formula (I) are used to prepare a medicament for the cosmetic, therapeutic and/or prophylactic treatment of actinic keratosis. More particularly, the actinic keratosis is selected from the group consisting of hypertrophic, atrophic, bowenoid, and acantholythic keratosis.

In this case, when the medicament is for the cosmetic, therapeutic and/or prophylactic treatment of actinic keratosis, 2,5-dihydroxybenzene derivatives of the invention may be used optionally and jointly with at least one of the following therapeutic agents: imiquimod, diclofenac, glycidic acid, trichloroacetic acid, colchicine, T4 endonuclease, 5-fluorouracil, isotretinoin, acitretin, cidofoir, 5-aminolevulinic acid, methyl aminolevulinate, hypericin, chemotherapeutic agent, a corticosteroid, an antibiotic, an analgesic, an immunomodulator, an immunosuppressant, an anti-angiogenic (including anti-VEGF, anti-FGF, anti-EGF and anti-HGF), a leukotriene modifier, an aminosalicylate, an anesthetic, a non-steroidal anti-inflammatory, a therapy of the solubilized interleukin receptor, a cytotoxic, inhibitors of tyrosin-kinase receptors, protein kinase C inhibitors, and combinations of two or more thereof.

In a particular embodiment, the therapeutic agent is selected from the group consisting of 5-aminolevulinic, methyl aminolevulinate and hypericine.

In another particular embodiment the therapeutic and/or prophylactic treatment of actinic keratosis further comprises photodynamic therapy, cryotherapy, curettage and surgery as a coadjuvant therapy.

In another particular embodiment, 2,5-dihydroxybenzenic derivatives of formula (I) are used to prepare a medicament for the cosmetic, therapeutic and/or prophylactic treatment of obesity, hirsutism, hypertricosis and viral warts.

In this particular case, when the medicament is for the cosmetic, therapeutic and/or prophylactic treatment of obesity, hirsutism, hypertricosis and viral warts, 2,5-dihydroxybenzenic derivatives of the invention may be used optionally and jointly with at least one of the following therapeutic agents: imiquimod, diclofenac, glycidic acid, trichloroacetic acid, colchicine, T4 endonuclease, 5-fluorouracil, isotretinoin, acitretin, statins, any other hypolypidemic agent and cidofoir.

Another aspect of the invention is that 2,5-dihydroxybenzene derivatives may be optionally used combined with each other. In this manner and as an example, it is possible to combine the dobesilate with the homogentisic, or the gentisic with the homogentisic, or a dobesilate ester derivative with the homogenisic, and the like in the same or in a different ratio. Said combinations may be in the same formulation or in formulations that would be used sequentially.

The $X^+$ cation in the compound of Formula (I) may be any physiologically acceptable cation known in the art, that includes but is not limited to those described in P. Heinrich Stahl, Camille G. Wermuth (eds.), "Handbook of Pharmaceutical Salts Properties, Selections and Use", Verlag Helvetica Chimica Acta, Zurich, Switzerland, Wiley-VCH, Weinheim, Germany, 2002.

The $X^+$ cation is typically selected in such a way that the general charge of Formula (I) is neutral.

In a particular embodiment of the invention Y is selected from —$SO_3H$, —$SO_3^-.X^+$, —$SO_3R_3$, —$CO_2H$, —$CO_2^-.X^+$ and —$CO_2R_3$.

In another particular embodiment, at least one of $R_9$ and $R_{9'}$ are, independently, a substituted or unsubstituted alkylsulfonyloxy group, a substituted or unsubstituted arylsulfonyloxy group, a substituted or unsubstituted alkylcarbonyloxy group or a substituted or unsubstituted arylcarbonyloxy group.

In another particular embodiment, $R_2$ is selected from methylcarbonyl, phenylsulfonyl, 4-methylphenylsulfonyl, benzylsulfonyl, benzyl and phenyl.

In another particular embodiment of the invention, $R_2$ is selected from acetyl (—$C(O)CH_3$), tosyl (—$SO_2$—$C_6H_4$—$CH_3$) or p-chlorophenoxyisobutyryl (—$C(O)$—$C(CH_3)_2$—$O$—$C6H_4Cl$).

In another particular embodiment of the invention, $R_3$ is selected from methyl, ethyl, isopropyl or $C_6H_5$—, more particularly form methyl and ethyl.

In a preferred embodiment of the invention, the inorganic cation is sodium, potassium, lithium, calcium, or magnesium.

In another preferred embodiment of the invention, the organic cation is $[NH_{4-p}R_p]^+$: wherein p is an integer between 0 and 4 and R is an alkyl group having one to six carbon atoms such as, for example, methyl, ethyl, n-propyl, i-propyl, t-butyl or n-pentyl.

In another preferred embodiment of the invention, the organic cation is the diethylamine $[H_2N^+(C_2H_5)_2]$, piperazine or pyridine group.

In another preferred embodiment of the invention, the compound of Formula (I) and acceptable salts thereof are:

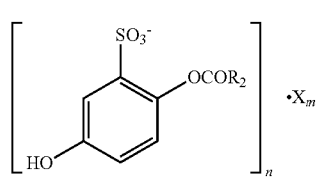

(1)

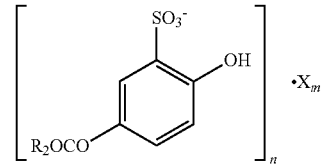

(2)

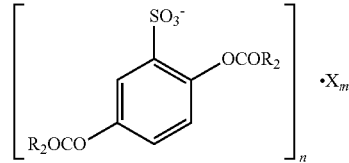

(3)

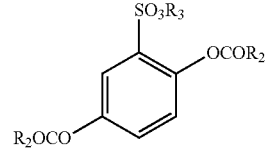

(4)

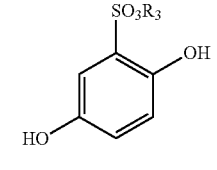

(5)

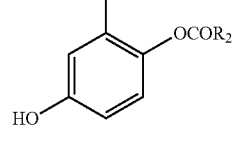

(6)

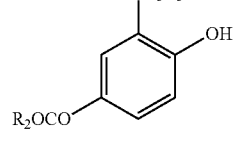

(7)

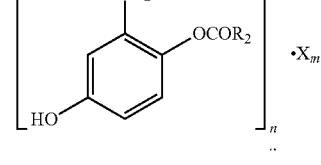

(8)

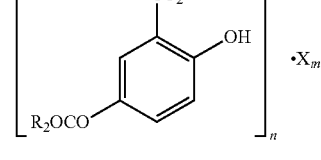

(9)

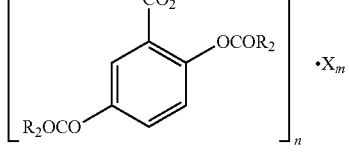

(10)

-continued
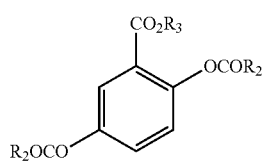 (11)
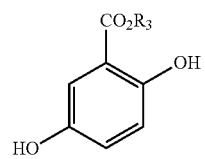 (12)
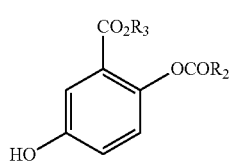 (13)
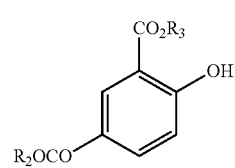 (14)
 (15)
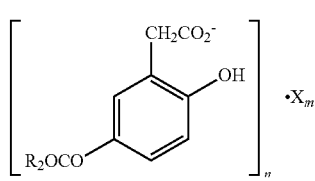 (16)
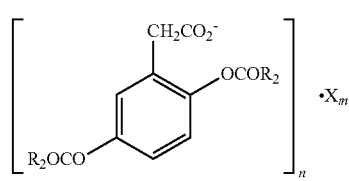 (19)
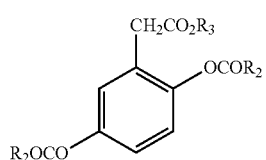 (20)
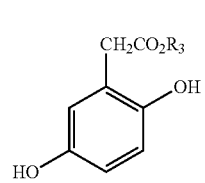 (21)
-continued
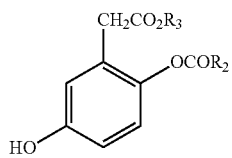 (22)
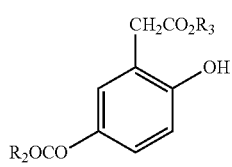 (23)
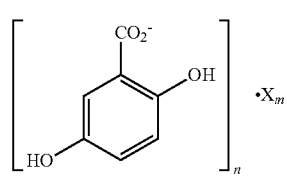 (24)
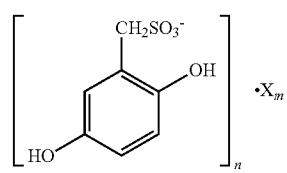 (25)
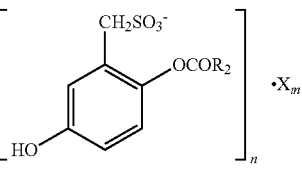 (26)
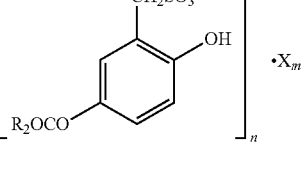 (27)
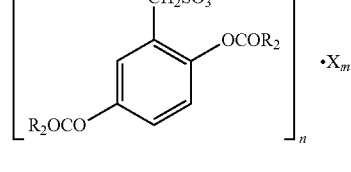 (28)
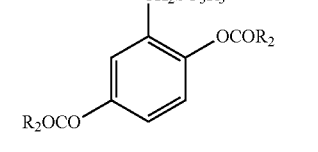 (29)
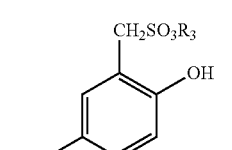 (30)

-continued

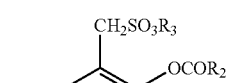
(31)

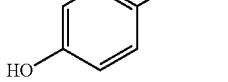
(32)

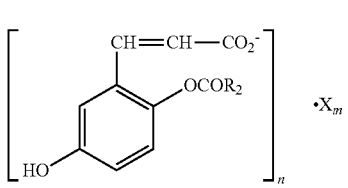
(33)

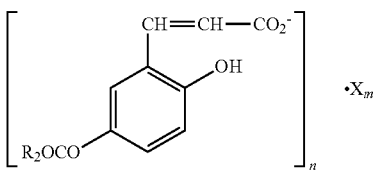
(34)

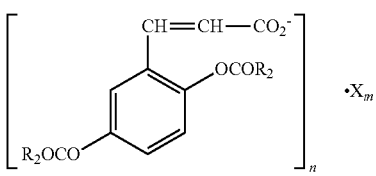
(35)

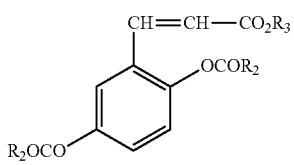
(36)

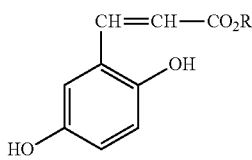
(37)

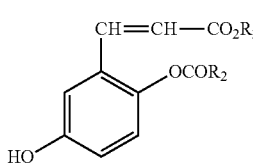
(38)

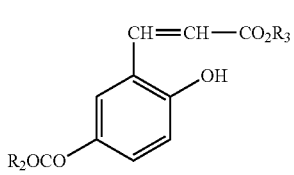
(39)

-continued

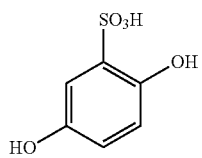
(40)

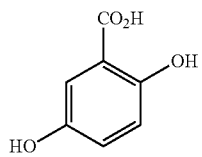
(41)

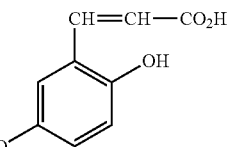
(42)

wherein:
n is a number selected from 1 and 2;
m is a number selected from 1 and 2; and
X, $R_2$ and $R_3$ are as defined in the present invention.

In a more preferred embodiment of the invention, the compound of Formula I is:
2,5-dihydroxybenzenesulfonic acid (Dobesilate),
5-hydroxy-2-{[(4-methylphenyl)sulfonyl]oxy}benzenesulfonic acid;
2-hydroxy-5-{[(4-methylphenyl)sulfonyl]oxy}benzenesulfonic acid;
2,5-bis{[(4-methylphenyl)sulfonyl]oxy}benzenesulfonic acid;
2-(acetyloxy)-5-hydroxybenzenesulfonic acid;
5-(acetyloxy)-2-hydroxybenzenesulfonic acid;
2,5-bis(acetyloxy)benzenesulfonic acid;
2-(benzyloxy)-5-hydroxybenzenesulfonic acid;
5-(benzyloxy)-2-hydroxybenzenesulfonic acid;
2,5-bis(benzyloxy)benzenesulfonic acid;
2,5-dihydroxybenzene homosulfonic acid (homodobesilate)
5-hydroxy-2-{[(4-methylphenyl)sulfonyl]oxy}benzenehomosulfonic acid;
2-hydroxy-5-{[(4-methylphenyl)sulfonyl]oxy}benzenehomosulfonic acid;
2,5-bis{[(4-methylphenyl)sulfonyl]oxy}benzenehomosulfonic acid;
2-(acetyloxy)-5-hydroxybenzenehomosulfonic acid;
5-(acetyloxy)-2-hydroxybenzenehomosulfonic acid;
2,5-bis(acetyloxy)benzenehomosulfonic acid;
2-(benzyloxy)-5-hydroxybenzenehomosulfonic acid;
5-(benzyloxy)-2-hydroxybenzenehomosulfonic acid;
2,5-bis(benzyloxy)benzenehomosulfonic acid;
2,5-dihydroxybenzoic acid (gentisic acid),
5-hydroxy-2-{[(4-methylphenyl)sulfonyl]oxy}benzoic acid;
2-hydroxy-5-{[(4-methylphenyl)sulfonyl]oxy}benzoic acid;
2,5-bis{[(4-methylphenyl)sulfonyl]oxy}benzoic acid;
2-(acetyloxy)-5-hydroxybenzoic acid;
5-(acetyloxy)-2-hydroxybenzoic acid;
2,5-bis(acetyloxy)benzoic acid;
2-(benzyloxy)-5-hydroxybenzoic acid;
5-(benzyloxy)-2-hydroxybenzoic acid;
2,5-bis(benzyloxy)benzoic acid;
2,5-dihydroxyhomobenzoic acid (homogentisic acid),
5-hydroxy-2-{[(4-methylphenyl)sulfonyl]oxy}homobenzoic acid;

2-hydroxy-5-{[(4-methylphenyl)sulfonyl]oxy}homobenzoic acid;
2,5-bis{[(4-methylphenyl)sulfonyl]oxy}homobenzoic acid;
2-(acetyloxy)-5-hydroxyhomobenzoic acid;
5-(acetyloxy)-2-hydroxyhomobenzoic acid;
2,5-bis(acetyloxy)homobenzoic acid;
2-(benzyloxy)-5-hydroxyhomobenzoic acid;
5-(benzyloxy)-2-hydroxyhomobenzoic acid;
2,5-bis(benzyloxy)homobenzoic acid;
3-(2,5-dihydroxyphenyl)-2-propenoic acid (2,5-dihydroxycinnamic acid);
3-(5-hydroxy-2-{[(4-methylphenyl)sulfonyl]oxy}phenyl)-2-propenoic acid;
3-(2-hydroxy-5-{[(4-methylphenyl)sulfonyl]oxy}phenyl)-2-propenoic acid;
3-(2,5-bis{[(4-methylphenyl)sulfonyl]oxy}phenyl)-2-propenoic acid;
3-(2-(acetyloxy)-5-hydroxyphenyl)-2-propenoic acid;
3-(5-(acetyloxy)-2-hydroxyphenyl)-2-propenoic acid;
3-(2,5-bis(acetyloxy)phenyl)-2-propenoic acid;
3-(2-(benzyloxy)-5-hydroxyphenyl)-2-propenoic acid;
3-(5-(benzyloxy)-2-hydroxyphenyl)-2-propenoic acid;
3-(2,5-bis(benzyloxy)phenyl)-2-propenoic acid;
and pharmaceutically acceptable salts, solvates and prodrugs thereof.

In a more preferred embodiment, the compound of Formula (I) is 2,5 dihydroxybenzenesulfonic (Dobesilate) or the ester derivatives or pharmaceutically acceptable salts thereof. Particularly preferred are the compounds 2-(acetyloxy)-5-hydroxybenzenesulfonic acid; 5-(acetyloxy)-2-hydroxybenzenesulfonic acid and 2,5-bis(acetyloxy)benzenesulfonic acid.

In another preferred embodiment, the compound of formula (I) is selected from the group consisting of:
calcium 2,5-dihydroxybenzenesulfonate (calcium Dobesilate);
potassium 2,5-dihydroxybenzenesulfonate (potassium Dobesilate);
magnesium 2,5-dihydroxybenzenesulfonate (magnesium Dobesilate);
diethylamine 2,5-dihydroxybenzenesulfonate (Ethamsylate).

Particularly preferred are calcium 2,5-dihydroxybenzenesulfonate (calcium dobesilate) and potassium 2,5-dihydroxybenzenesilfonate (potassium dobesilate).

In another preferred embodiment, the compounds of formula (I) are in the form of esters at position 1, in particular methyl and ethyl esters.

The compounds of Formula (I) may be synthesized by one skilled in the art using conventional and commercially available methods. The synthesis of the compounds of Formula (I) is disclosed in, for example, U.S. Pat. No. 5,082,941; and "The Merck Index" 13th. edition, Merck & Co., R. Railway, N.J., USA, 2001; U.S. Pat. Nos. 5,082,841, 4,814,110, 4,613,332 and 4,115,648; the disclosures which are incorporated herein by reference in their entirety.

Compounds of Formula (I) also may be in the form of solvates, particularly in the form of hydrates. The preparation of the compounds of Formula (I), as well as the solvates thereof may be carried out by one skilled in the art using conventional methods and commercially available reagents.

Even as it has been previously mentioned in one of the preferred embodiments with respect to the definition of $X^+$ cation, the scope of the present invention encompasses any salt thereof, especially any pharmaceutically acceptable salt of the compound. The phrase "pharmaceutically acceptable salts" includes metal salts or the addition salts that may be used in pharmaceutical forms. For example, the pharmaceutically acceptable salts of the compounds provided herein may be acid addition salts, base addition salts or metal salts and they may be synthesized from the parenteral compounds containing a base or acid residue using conventional chemical processes. Generally, those salts are prepared, for example, by the reaction of free base or acid forms of these compounds with a stoichiometric amount of the appropriate base or acid in water or in an organic solvent, or in a mixture of both. Generally, non aqueous mediums such as ether, ethyl acetate, ethanol, isopropanol or acetonitrile are preferred. The examples of acid addition salts include addition salts of mineral acids such as, for example, hydrochloride, bromhydrate, iodide hydrate, sulfate, nitrate, phosphate, addition salts of organic acids such as, for example, acetate, maleate, fumarate, citrate, oxalate, succinate, tartrate, malate, mandelate, methanesulfonate and p-toluenesulfonate. The examples of alkali addition salts include inorganic salts such as, for example, ammonium salts and organic alkaline salts such as, for example, diethylamine, ethylenediamine, ethanolamine, N,N-dialkylenethanolamine, triethanolamine, glutamine and basic amino acid salts. The examples of metal salts include, for example, sodium, potassium, calcium, magnesium, aluminum, and lithium salts.

In some embodiments, the invention provides a composition comprising an ester of Formula I, especially an ester of dobesilate, such as 2-acetyloxy-5-hydroxybenzenesulfonic acid, 5-acetyloxy-2-hydroxybenzenesulfonic acid, or 2,5-bis-acetyloxybenzenesulfonic acid. In some embodiments, it will be desirable to formulate a composition of the invention with an active agent such as an ester of dobesilate, for example, where the ester demonstrates greater therapeutic efficacy than the parent compound in the treatment or prevention of a condition described herein. In other embodiments, the invention encompasses the use of an ester of dobesilate as a prodrug, for example, to treat a condition described herein, wherein the ester is metabolized to the parent compound in a patient to achieve therapeutic efficacy in the patient.

The phrase "pharmaceutically acceptable" refers to physiologically tolerable molecular entities and compositions which do not typically produce an allergic or similar adverse reaction, such as gastric upset, dizziness, and the like, when administered to a human. Preferably, as used herein, the term "pharmaceutically acceptable" means that it is approved by a regulatory agent of the Federal or a state government or listed in the U.S. Pharmacopeia or other generally recognized pharmacopoeia as suitable for use in animals, and more particularly, in humans.

It would be obvious to those skilled in the art that the scope of the present invention also encompasses salts that are not pharmaceutically acceptable as possible media to obtain pharmaceutically acceptable salts.

As used herein, the term "solvate" shall refer to any form of the active compound according to the invention that exhibits another molecule (most probably, a polar solvent) bound to it through a non-covalent bond. Examples of solvates include hydrates and alcoholates, preferably, $C_1$-$C_6$ alcoholates, for example, methanolate.

The pharmaceutically acceptable salts of Formula (I) may be prepared from organic or inorganic acids or bases by conventional methods through the reaction of the appropriate acid or base with the compound.

A medicament comprising a compound of formula (I) of the invention may be presented in any suitable form for administration, for example, for systemic, transdermal, oral, parenteral, buccal, nasal (e.g., by inhalation), topical, rectal, or intravaginal administration; therefore, a medicament of the invention may include the acceptable pharmaceutical excipients or vehicles necessary to be formulated in the desired form of administration. In a preferred embodiment, the pharmaceutical composition is administered topically.

Thus, in one preferred aspect, the present invention refers to a method for the treatment and/or prophylaxis of actinic keratosis, obesity due to excessive adipogenesis, hirsutism, hypertricosis, viral warts, skin wrinkles, skin pigmentation and/or skin hyperpigmentation in a patient in need of the treatment and it comprises the administration to the patient of an effective amount of the described compounds and/or compositions of Formula (I).

In other embodiments, the application of the 2,5-dihydroxybenzene compounds represented by Formula (I) may be made independently or, in a preferred aspect, simultaneously with the use of equivalent or different mixes of other 2,5-dihydroxybenzene compounds represented by Formula (I) (including pharmaceutically acceptable salts and esters) and these compounds may be in the same formulation or in independent formulations that would be simultaneously or sequentially administered.

In another aspect, the present invention refers to a cosmetic product comprising 2,5-dihydroxybenzene derivatives or any of the pharmaceutically acceptable salts thereof represented by Formula (I).

In an embodiment, the present invention refers to a cosmetic product that comprises 2,5-dihydroxybenzene derivatives or any of the pharmaceutically acceptable salts thereof represented by Formula (I) characterized in that the compound of Formula (I) is 2,5-dihydroxybenzenesulfonic acid (dobesilate) or pharmaceutically acceptable salts or esters thereof.

In another embodiment, the present invention refers to a cosmetic product that comprises 2,5-dihydroxybenzene derivatives or any of the pharmaceutically acceptable salts thereof represented by Formula (I) characterized in that the compound of Formula (I) is 2,5-dihydroxybenzoic acid (gentisic acid) or pharmaceutically acceptable salts or esters thereof.

In another embodiment, the present invention refers to a cosmetic product that comprises 2,5-dihydroxybenzene derivatives or any of the pharmaceutically acceptable salts thereof represented by Formula (I) characterized in that the compound of Formula (I) is 2,5-dihydroxyphenyl acetic acid (homogentisic acid) or pharmaceutically acceptable salts or esters thereof.

In another embodiment, the present invention refers to a cosmetic product that comprises 2,5-dihydroxybenzene derivatives or any of the pharmaceutically acceptable salts thereof represented by Formula (I) characterized in that the compound of Formula (I) is 3-(2,5-dihydroxyphenyl)-2-propenoic acid (dihydroxycinnamic acid) or pharmaceutically acceptable salts or esters thereof.

In another embodiment, the present invention refers to a cosmetic product that comprises 2,5-dihydroxybenzene derivatives or any of the pharmaceutically acceptable salts thereof represented by Formula (I) characterized in that the compound of Formula (I) is 2,5-dihydroxybenzene homosulfonic acid (homodobesilate) or pharmaceutically acceptable salts or esters thereof.

In another embodiment, the present invention refers to a cosmetic product characterized in that the compound of Formula (I) is the 2,5-dihydroxybenzenesulfonic acid (dobesilate) or the pharmaceutically acceptable salts or esters thereof characterized in that it consists of a formulation for antiphotoaging or photoprotection of the skin.

In another embodiment, the present invention refers to a cosmetic product characterized in that the compound of Formula (I) is 2,5-dihydroxybenzenesulfonic acid (dobesilate) or the pharmaceutically acceptable salts or esters thereof characterized in that it consists of a formulation for lightening skin hyperpigmentation.

In another embodiment, the present invention refers to a cosmetic product characterized in that the compound of Formula (I) is 2,5-dihydroxybenzenesulfonic acid (dobesilate) or the pharmaceutically acceptable salts or esters thereof characterized in that is consists of a formulation to treat hirsutism and/or hypertricosis.

In another embodiment, the present invention refers to a cosmetic product characterized in that the compound of Formula (I) is the 2,5-dihydroxybenzenesulfonic acid (dobesilate) or the pharmaceutically acceptable salts or esters thereof characterized in that it consists of a formulation to treat viral warts and/or actinic keratosis.

In another embodiment, the present invention refers to a cosmetic product characterized in that the compound of Formula (I) is the 2,5-dihydroxybenzenesulfonic acid (dobesilate) or the pharmaceutically acceptable salts or esters thereof characterized in that it consists of a formulation for the aesthetical treatment of obesity.

In another embodiment, the present invention refers to a cosmetic product characterized in that the compound of Formula (I) is the 2,5-dihydroxybenzenesulfonic acid (dobesilate) or the pharmaceutically acceptable salts or esters thereof characterized in that it consists of a formulation to be therapeutically used in skin wrinkles.

In another embodiment, the present invention refers to a cosmetic product characterized in that the compound of Formula (I) is the gentisic acid or the homogentisic acid or the pharmaceutically acceptable salts or esters thereof characterized in that it consists of a formulation for the aesthetic treatment of obesity due to excess adipogenesis, for the treatment of hirsutism, hypertricosis, viral warts and actinic keratosis.

In another embodiment, the present invention refers to a cosmetic product according to any of the previous aspects characterized in that it is presented in the form of cream, ointment, unguent, microsomes, bandages, or patches.

In another embodiment, the present invention refers to a cosmetic product according to any of the previous aspects characterized in that it contains an amount of 5% of 2,5-dihydroxybenzene sulfonic acid, potassium salt.

In another embodiment, the present invention refers to a cosmetic product according to any of the previous aspects characterized in that it comprises as excipients: cetyl alcohol (2.5%), stearyl alcohol (2.5%), liquid vaseline (30%), filante vaseline (20%), sorbitan monooleate (5%) and distilled water (q.s. to 100 g).

In another embodiment, the present invention refers to the use of 2,5-dihydroxybenzene derivatives or any of the pharmaceutically acceptable esters or salts thereof represented by Formula (I) to prepare a formulation intended to be cosmetically used.

In another embodiment, the present invention refers to a method for cosmetic or therapeutic treatment of any of the indications comprised in the following group: obesity due to excess adipogenesis, hirsutism, hypertricosis, viral warts, and/or actinic keratosis comprising the administration to a patient of a composition comprising a compound of Formula (I).

In one embodiment, the present invention refers to the use of 2,5-dihydroxybenzene derivatives or any pharmaceutically acceptable esters or salts thereof represented by Formula (I)

wherein the compound of Formula (I) is 2,5-dihydroxybenzensulfonic acid (dobesilate) or the salts or esters thereof, to prepare a drug or medicine intended for the cosmetic or therapeutic treatment of obesity due to excess adipogenesis, actinic keratosis, to treat hirsutism and hypertricosis and viral warts.

In one embodiment, the present invention refers to the use of 2,5-dihydroxybenzene derivatives or any pharmaceutically acceptable esters or salts thereof represented by Formula (I) wherein the compound of Formula (I) is gentisic acid or the salts or esters thereof, to prepare a drug or medicine intended for the cosmetic or therapeutic treatment of obesity due to excess adipogenesis, actinic keratosis, to treat hirsutism and hypertricosis and viral warts.

In one embodiment, the present invention refers to the use of 2,5-dihydroxybenzeneic derivatives or any pharmaceutically acceptable esters or salts thereof represented by Formula (I) wherein the compound of Formula (I) is 3-(2,5-dihydroxyphenyl)-2-propenoic acid (dihydroxycinnamic acid) or the salts or esters thereof, to prepare a drug or medicine intended for the cosmetic or therapeutic treatment of obesity due to excess adipogenesis, actinic keratosis, to treat hirsutism and hypertricosis and viral warts.

In one embodiment, the present invention refers to the use of 2,5-dihydroxybenzene derivatives or any pharmaceutically acceptable esters or salts thereof represented by Formula (I) wherein the compound of Formula (I) is homodobesilate or the salts or esters thereof, to prepare a drug or medicine intended for the cosmetic or therapeutic treatment of obesity due excess adipogenesis, actinic keratosis, to treat hirsutism and hypertricosis and viral warts.

In another embodiment, the present invention refers to the use of 2,5-dihydroxybenzene derivatives or any pharmaceutically acceptable esters or salts thereof represented by Formula (I) wherein the compound of Formula (I) is 2,5-dihydroxyphenyl acetic acid (homogentisic acid) or the salts or esters thereof, to prepare a drug or medicine intended for the cosmetic or therapeutic treatment of obesity due to excess adipogenesis, actinic keratosis, to treat hirsutism and hypertricosis, skin wrinkles, viral warts, and pathologies associated with cutaneous photoaging, such as, for example, skin pigmentation, skin hyperpigmentation or solar lentigos.

In one embodiment, the present invention refers to a method for cosmetic treatment of any of the indications comprised in the following group: skin wrinkles, hirsutism, hypertricosis, viral warts, actinic keratosis or obesity wherein the compound of Formula (I) is 2,5-dihydroxybenzenesulfonic (dobesilate) or the salts or esters thereof.

Similarly, as previously explained in the description, in one aspect, the present invention refers to the use of 2,5-dihydroxybenzene derivatives, the pharmaceutically acceptable esters or salts thereof represented by Formula (I) to prepare a drug, medicine or composition intended for the cosmetic treatment of any of the following diseases: obesity due to excess adipogenesis, actinic keratosis, viral warts, hypertricosis or hirsutism.

In another aspect, the present invention refers to the use of 2,5-dihydroxybenzene derivatives represented by Formula (I) wherein the compound of Formula (I) is 2,5-dihydroxybenzenesulfonic (dobesilate) or the pharmaceutically acceptable esters or salts thereof to prepare a drug, medicine or composition intended for the cosmetic treatment of any of the following diseases: skin wrinkles or actinic keratosis.

Another aspect of the present invention refers to a method for cosmetic treatment method of any of the diseases comprised in the following group: obesity due to excess adipogenesis, actinic keratosis, viral warts, skin wrinkes, hypertricosis or hirsutism comprising the administration to a patient of a composition comprising Formula (I), or the pharmaceutically acceptable salts or esters thereof.

Another aspect of the present invention refers to a method for therapeutic treatment of any of the diseases comprised in the following group: obesity due to excess adipogenesis, actinic keratosis, skin wrinkles, viral warts, hypertricosis, hirsutism, diseases associated to skin photoaging, such as, for example, skin pigmentation, skin hyperpigmentation or solar lentigos consisting in the administration to a patient of a composition comprising Formula (I), or the pharmaceutically acceptable salts or esters thereof.

The duration of treatment will typically depend on the particular condition, its severity, the condition of the patient, and the like, and will readily be determined by one of skill in the art. Illustrative courses of therapy include 1 week, 2 weeks, 3 weeks, 4 weeks, 5 weeks, 6 weeks, 7 weeks, 8 weeks, 9 weeks, 10 weeks, 11 weeks, 12 weeks, 3.5 months, 4 months, 4.5 months, 5 months, 6 months, 9 months, a year, or longer as needed.

In treating a subject suffering from a disorder described herein, treatment may be continued until at least a 10% improvement is effected in a symptom associated with the condition. In other embodiments, treatment is continued until the subject in need of such treatment experiences an improvement of at least about 20%, at least about 30%, at least about 40%, preferably at least about 50%, preferably at least about 60%, more preferably at least about 70%, more preferably at least about 80%, even more preferably 90% or greater in a symptom associated with a disorder described herein.

In a particular embodiment of the invention, a compound of formula (I) is administered at least once per week. In other embodiments, a compound of formula (I) is administered at least once per day. In yet other embodiments, a compound of formula (I) is administered twice per day. In another particular embodiment, a compound of formula (I) is administered over a period of at least about one week. In other embodiments, a compound of formula (I) is administered over a period of at least about four weeks.

Therapeutic amounts can be empirically determined and will vary with the particular condition being treated, the subject, the particular formulation components, dosage form, and the like.

In a particular embodiment, a compound of formula (I) is present in a pharmaceutical composition in an amount of at least about 1% w/w. In other embodiments, a compound of formula (I) is present in a pharmaceutical composition in an amount of at least about 2.5% w/w, at least about 5% w/w, at least about 10% w/w, or at least about 15% w/w.

In one aspect of the invention, the inventive 2,5-dihydroxybenzene compounds of Formula (I) may be administered topically in a formulation comprising from about 0.001% to about 30% (w/w) of the inventive 2,5-dihydroxybenzene compounds: of Formula (I). In a preferred aspect of the invention, the inventive 2,5-dihydroxybenzene compounds: of Formula (I) may be administered topically in a formulation comprising from about 0.01% to about 20% (w/w) of the inventive 2,5-dihydroxybenzene compounds: of Formula (I). In another preferred aspect of the invention, the inventive 2,5-dihydroxybenzene compounds: of Formula (I) may be administered topically in a formulation comprising from about 0.1% to about 15 (w/w) of the inventive 2,5-dihydroxybenzene compounds: of Formula (I). In a preferred aspect of the invention, the inventive 2,5-dihydroxybenzene compounds: of Formula (I) may be administered topically in a formulation comprising from about 0.5% to about 10% (w/w) of the inventive 2,5-dihydroxybenzene compounds: of Formula (I). In another preferred aspect of the invention, the inventive 2,5-dihydroxybenzene compounds: of Formula (I) may be administered topically in a formulation comprising from about 1% to about 5% (w/w) of the inventive 2,5-dihydroxybenzene compounds: of Formula (I). In another preferred aspect of the invention, the inventive 2,5-dihydroxybenzene derivatives: of Formula (I) may be administered topically in a formulation comprising from about 2.5% to about 4% (w/w) of the inventive 2,5-dihydroxybenzene compounds: of Formula (I). The topic formulation of the compounds comprised in the inventive 2,5-dihydroxybenzene compounds: of Formula (I) may be administered as a single dose once a day or in multiple doses several times a day. In a preferred aspect of the invention, the topical formulation which comprises 30%, 20%, 15%, 10%, 5%, 2.5%, 1%, 0.5%, 0.1% or 0.001% of the inventive 2,5 dihydroxybenzene compounds: of Formula (I), is administered four times a day. In another preferred aspect of the invention, the topical formulation which comprises about 30%, 20%, 15%, 10%, 5%, 2.5%, 1%, 0.5%, 0.1% or 0.001% of the inventive 2,5 dihydroxybenzene compounds: of Formula (I), is administered three times a day. In another preferred aspect of the invention, the topical formulation which comprises about 30%, 20%, 15%, 10%, 5%, 2.5%, 1%, 0.5%, 0.1% or 0.001% of the inventive 2,5 dihydroxybenzene compounds: of Formula (I), is administered twice a day. In another preferred aspect of the invention, the topical formulation which comprises about 30%, 20%, 15%, 10%, 5%, 2.5%, 1%, 0.5%, 0.1% or 0.001% of the inventive 2,5 dihydroxybenzene compounds: of Formula (I), is administered once a day.

Topical Compositions

The product of the present invention is useful for topical application on the skin. The compositions comprise an effective amount of the inventive compounds: of Formula (I), preferably from about 0.001 to 30%. Furthermore, the composition comprises a pharmaceutical acceptable vehicle. The appropriate vehicles remain in the place of application on the skin forming a continuous film resistant to water immersion and perspiration. Generally, the vehicle is organic and capable of containing the formulation of the invention in a diluted or dispersed form. Lotions, creams, solutions, gels and solids are the usual physical forms of the composition.

Topical application means depositing or spreading the compound and the compositions over the epidermic tissue (including skin and oral, gingival, nasal, etc. tissues).

Lotions

Lotions contain from about 0.001% to about 30% of the inventive compounds of Formula: (I) from 1% to 25% of an emollient and the appropriate amount of water. Examples of emollients are:

I. Hydrocarbon waxes and oils such as mineral oils, petrolatum, paraffin, ceresin, microcrystalline wax, polyethylene and perhydrosqualene.
II. Silicone oils such as dimethylpolysiloxanes, methylphenylpolysiloxanes and water-soluble and alcohol-soluble glycol-silicone copolymers.
III. Triglycerides, such as animal and vegetable fats and oils. Examples include, but are not limited to, castor oil, cod liver oil, corn oil, olive oil, almond oil, palm oil, sesame oil, cotton seed oil and soybean oil.
IV. Acetoglyceride esters, such as acetylated monoglycerides.
V. Ethoxylated glycerides, such as ethoxylated glycerol monostearate.
VI. Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristoyl lactate and cetyl lactate.
VII. Alkenyl esters of fatty acids having 10 to 20 carbon atoms. Examples thereof include, but are not limited to, oleyl myristate, oleyl stearate and oleyl oleate.
VIII. Fatty acids having 10 to 20 carbon atoms. Suitable examples include, but are not limited to, pelargonic, lauric, myristic, palmitic, stearic, isostearic, hydroxystearic, oleic, linoleic, ricinoleic, arachidonic, behenic and erucic acids.
IX. Fatty alcohols having 10 to 20 carbon atoms. Lauryl, myristoyl, palmitoyl, stearyl, isostearyl, hydroxystearyl, oleyl, ricinoleyl, behenyl, erucyl and 2-octyl dodecanol alcohols are appropriate examples of fatty alcohols.
X. Fatty alcohol ethers. Ethoxylated fatty alcohols having 10 to 20 carbon atoms include, but are not limited to, lauryl, cetyl, stearyl, isostearyl, oleyl and cholesterol alcohols having attached thereto from 1 to 50 ethylene oxide groups or 1 to 50 propylene oxide groups.
XI. Ether-esters, such as fatty acid esters of ethoxylated fatty alcohols.
XII. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleates, lanolin alcohols ricinoleate, acetate of lanolin alcohols ricinoleate, hydrogenolysis of lanolin, and liquid or semisolid lanolin absorption bases are illustrative examples of lanolin derived emollients.
XIII. Polyhydric alcohols and polyether derivatives. Propylene glycol, dipropylene glycol, polypropylene glycol 2000 and 4000, polyoxyethylene polypropylene glycols, glycerol, ethoxylated glycerol, propoxylated glycerol, sorbitol, ethoxylated sorbitol, hydroxypropyl sorbitol, polyethylene glycol 200-6000, methoxy polyethylene glycols 350, 550, 750, 2000, 5000, poly (ethylene oxide) homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), and polyoxypropylene derivatives of trimethylolpropane are suitable examples.
XIV. Polyhydric alcohol esters. Mono- and di-acyl esters of ethylene glycol, mono- and di-acyl esters of diethylene glycol, mono- and di-acyl esters of polyethylene glycol (200-6000), mono- and di-acyl esters of propylene glycol, polypropylene glycol 2000 monooleate, polypropylene glycol 2000 monostearate, ethoxylated propylene glycol monostearate, mono- and di-acyl esters of glycerol, poly-acyl esters of poly glycerol, ethoxylated glycerol monostearate, 1,3-butylene glycol monostearate, 1,3-butylene glycol distearate, acyl ester of polyoxyethylene polyol, acyl esters of sorbitan, and acyl esters of polyoxyethylene sorbitan are suitable examples.
XV. Waxes such as beeswax, spermaceti, myristoyl myristate and stearyl stearate.
XVI. Beeswax derivatives, such as polyoxyethylene sorbitol beeswax. These are reaction products of beeswax with ethoxylated sorbitol of varying ethylene oxide content that form a mixture of ether-esters.

XVII. Vegetable waxes, including, but not limited to, carnauba and candelilla waxes.

XVIII. Phospholipids such as lecithin and derivatives.

XIX. Sterols. Examples include, but are not limited to, cholesterol and acyl esters of cholesterol.

XX. Amides, such as fatty acid amides, ethoxylated acyl amides and solid fatty acid alkanolamides.

The lotions of the invention would further contain from 1% to 30% of an emulsifier. The emulsifiers can be anionic, cationic or non-ionic. Examples of non-ionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbons in the alkyl chain condensed with 2 to 20 moles of ethylene oxide, mono- and di-acyl esters of ethylene glycol, wherein the fatty acid contains from 10 to 20 carbons, monoglycerides wherein the fatty acid contains from 10 to 20 carbons, diethylene glycol, polyethylene glycols of molecular weight 200 to 6000, polypropylene glycol of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, fatty acids saponified (soaps) with potassium, sodium, or triethanolamine, wherein the fatty acid contains from 10 to 20 carbons. Other suitable anionic emulsifiers include, but are not limited to, alkali metals, ammonium or substituted ammonium with alkyl sulfates, alkyl arylsulfonates and alkyl ethoxy ether sulfonates having 10 to 30 carbons in the alkyl chain and from 1 to 50 ethylene oxide units. Suitable cationic emulsifiers include quaternary ammonium and morpholinium and pyridinium compounds.

Some emollients previously described also have emulsifying properties. When a lotion contains one of these emollients, an additional emulsifier is not needed, though it can be included in the formulation.

The balance of the composition is water. The lotions are formulated by simply admixing all of the components together. Preferably, the compounds of Formula I are dissolved in the emollient and the resulting mixture is added into the water. Optional components such as the emulsifier or common additives may be included in the composition. A common additive is a thickening agent included at a level of 1% to 30% by weight of the composition. Examples of suitable thickening agents are: Cross-linked carboxypolymethylene polymers, methyl cellulose, polyethylene glycols, gums and bentonite.

Creams

The compositions of the present invention may be also formulated in the form of a cream. Creams contain from 0.001% to 30% of the inventive compounds of Formula (I), from 5% to 50% of an emollient and the remainder is water. The emollients, as described above, can also be used in the cream formulation. Optionally, the cream may contain an emulsifier at a level from 3% to 50%. The previously described emulsifiers would also be adequate in this case.

Solutions

The compositions of the present invention may also be formulated in the form of a solution.

Solutions contain from 0.001% to 30% of the inventive compounds: of Formula (I), and the adequate amount of an organic solvent. Organic substances useful as the solvent or a part of the solvent system are as follows: propylene glycol, polyethylene glycol (200-600), polypropylene glycol (425-2025), glycerine, sorbitol esters, 1,2,6-hexanetriol, ethanol, isopropanol, diethyl tartrate, butanediol, and mixtures thereof. Such solvent systems can also contain water. These compositions are applied on the skin in the form of a solution, or solutions are formulated in the form of aerosol and applied on the skin as a spray. Compositions in the form of aerosol additionally contain from 25% to 80% of a suitable propellant. Examples of propellants include, but are not limited to: chlorinated, fluorinated and fluorochlorinated low molecular weight hydrocarbons. Nitrous oxide and carbon dioxide are also used as propellant gases. Enough quantity to expel the content of the cartridge is used.

Gels

The composition in the form of gel might be simply obtained by the addition of a suitable thickening agent to the composition in the form of a solution as described above. Suitable thickening agents have been described in the chapter referring to lotions.

Gel formulations contain from about 0.001% to about 30% of the compounds of Formula (I), 5% to 75% of a suitable organic solvent, 0.5% to 20% of a suitable thickening agent and the required amount of water.

Solids

The compositions in the present invention may also be formulated in solid form. Such forms have the shape of a bar intended for the application on the lips or other parts of the body. These compositions contain from about 0.001% to about 30% of the inventive compounds: of Formula (I), and from about 50% to about 98% of an emollient such as the one already described. The composition may be further contain from about 1% to about 20% of a suitable thickening agent, such as those already described, and, optionally, emulsifiers and water.

Additives usually found in topical compositions, such as preservatives (for example, methyl and ethyl paraben), dyes and perfumes may be included in any of the formulations described herein.

Application Method

The effective amount of compounds of Formula (I) used topically will vary according to the specific circumstances of application, the duration of exposure and similar considerations. Generally, the amount will vary from 0.01 microgram to 50 milligrams of the compounds of Formula (I), per square centimeter of the epidermis area. The amount of topical composition (the compounds of Formula (I) and the vehicle) applied on the affected area may be easily determined according to the amount of compounds of Formula (I) contained therein.

Kits

In yet other embodiments, the invention provides a kit or package comprising a compound of formula (I), in packaged form, accompanied by instructions for use. The compound of formula (I) may be packaged in any manner suitable for administration, so long as the packaging, when considered along with the instructions for administration, indicates the manner in which the compound of formula (I) is to be administered.

For example, a kit may comprise a compound of formula (I) in unit dosage form, along with instructions for use. For example, such instructions may indicate that administration of a compound of formula (I) is useful in the treatment of actinic keratosis. The compound of formula (I) may be packaged in any manner suitable for administration. For example, when the compound of formula (I) is in oral dosage form, e.g., is in the form of a coated tablet, then the kit may comprise a sealed container of coated tablets, blister strips containing the tablets, or the like.

Various embodiments according to the above may be readily envisioned, and would depend upon the particular dosage form, recommended dosage, intended patient population, and the like. The packaging may be in any form commonly employed for the packaging of pharmaceuticals, and may utilize any of a number of features such as different colors, wrapping, tamper-resistant packaging, blister packs or strips, and the like.

The following non-limiting examples further describe and enable one of ordinary skill in the art to make and use the present invention.

EXAMPLES

Example 1

Assay of 2,5-dihydroxybenzenesulfonic acid on photoaged skin

In this study, 2,5-dihydroxybenzenesulfonic acid, potassium salt, formulated as 5% by weight in the form of cream has been used, since this type of formulation is a habitual procedure for topical treatments of the skin. Distilled water has been used as the aqueous phase of the cream. The oil phase thereof may comprise cetyl alcohol, stearyl alcohol or vaseline. Span (sorbitan monooleate) is an effective emulsifier to make the cream.

The following example illustrates the formulation of an effective cream for the topical treatment of skin photoaging and must not be construed as a limitation of the scope of the invention.

Active principle: 2,5-dihydroxybenzenesulfonic acid, potassium salt, 5% by weight. Excipients: cetyl alcohol (2.5%), stearyl alcohol (2.5%), liquid vaseline (30%), white soft vaseline (20%), sorbitan monooleate (5%) and distilled water (q.s. to 100 g).

Continuous topical treatment of human photoaged skin with this cream (twice a day for 3 months) (FIG. 1A) results in a reduction of the wrinkles and the disappearance of actinic lentigo areas, as shown in FIG. 1B. Lightening of skin hyperpigmentation after the application of 2,5-dihydroxybenzenesulfonic acid may justify the use thereof to treat melanic dyschromia with hyperpigmentation as occurs, among other pathologies, in the Mongolian spot, the nevus of Ota, the nevus of Ito, the nevus of Becker, ephelides (freckles), the lentigo malign melanoma, the café-au-lait macules or the melasma (chloasma).

Example 2

Figure 2:
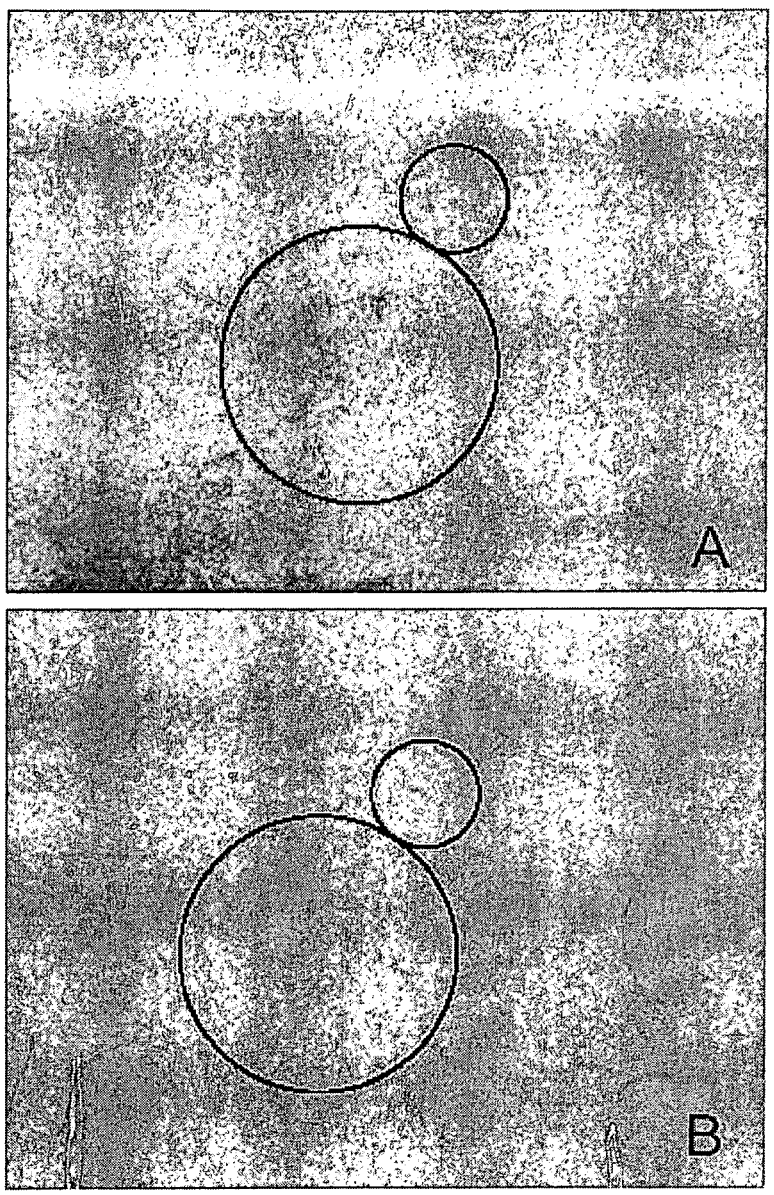
FIG. 2. The topical treatment with a cream containing 5% 2,5-dihydroxybenzenesulfonic acid (twice a day for 11 days) on human skin (basal conditions shown in FIG. 2A) produces a reduction in the seborrheic keratosis (big circle) as well as in the viral warts (small circle), as shown in FIG. 2B.

Effect of 2,5-dihydroxybenzenesulfonate on seborrheic keratosis, actinic keratosis and viral warts Topical treatment with the above described cream (twice a day for 11 days) of human skin (basal conditions shown in FIG. 2A) results in a reduction of seborrheic keratosis (big circle) as well as of viral warts (small circle), as shown in FIG. 2B.

Figure 3:
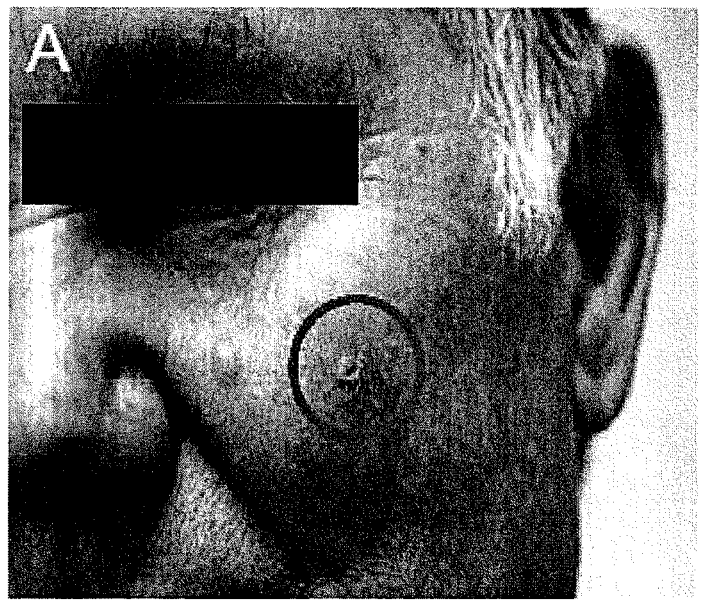
FIG. 3. Appearance of a patient's facial seborrheic keratosis before being treated (A) and after topical treatment of the affected skin area with an emulsion containing 2.5% 2,5-dihydroxybenzenesulfonic acid for 4 weeks (B). There is a reduction of the seborrheic keratosis.
Figure 3:
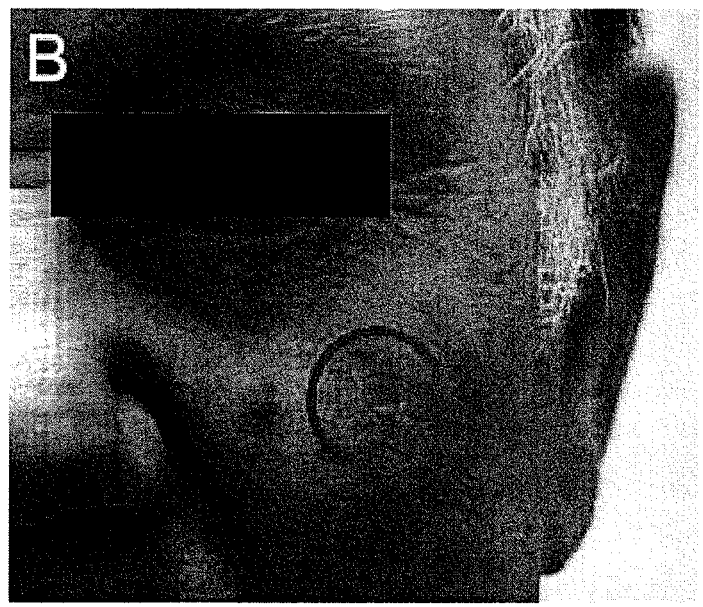

Another example of the effect of 2,5-dihydroxybenzenesulfonate on seborrheic keratosis is shown in FIG. 3, wherein the seborrheic keratosis is reduced due to the topical treatment on the affected area for 4 weeks, twice a day, with an emulsion containing the 2,5-dihydroxybenzenesulfonic acid, 2.5% by weight.

Figure 4:
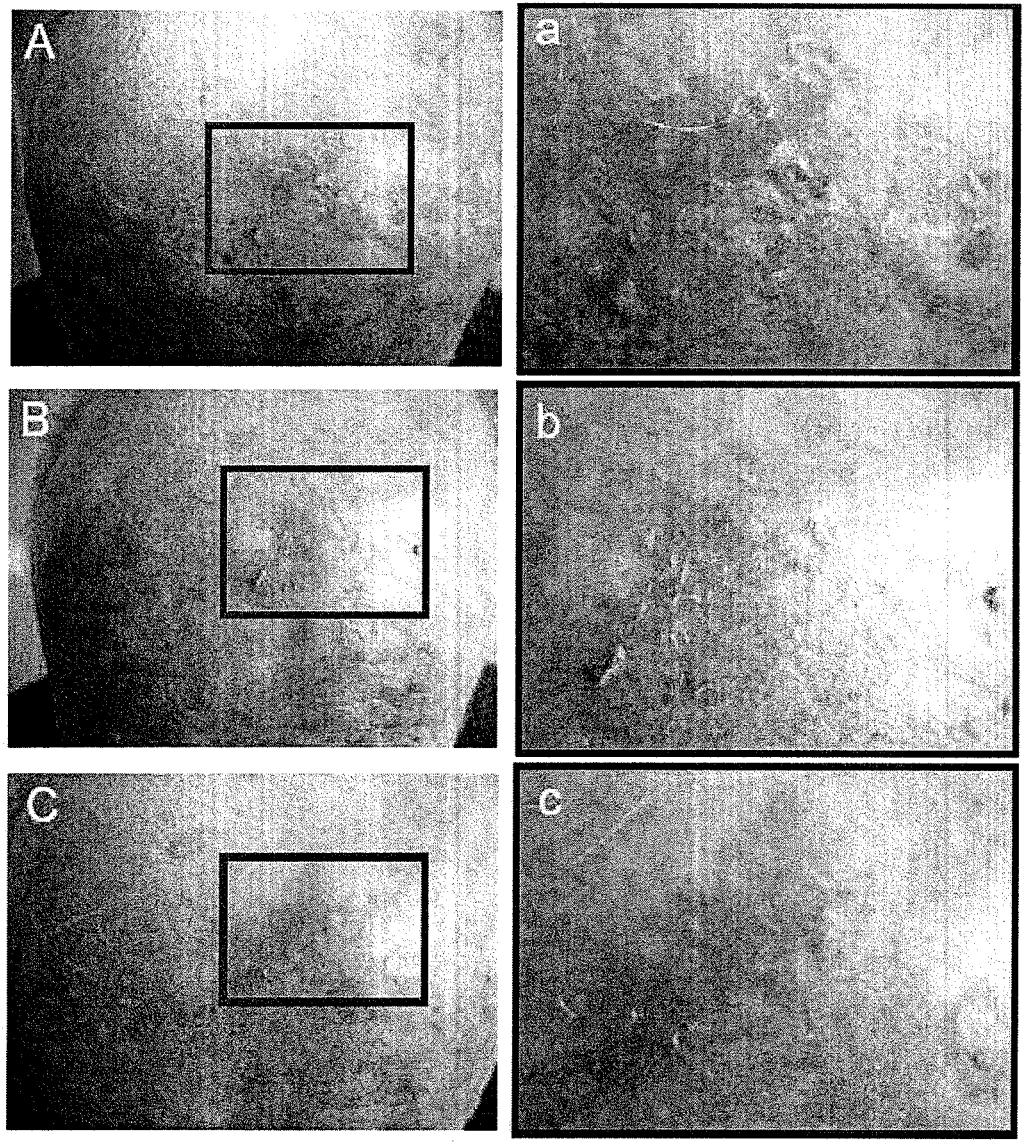
FIG. 4. Development of actinic keratosis in the scalp of a patient before being treated (A, a), after topical treatment of the affected skin area with an emulsion containing 2.5% 2,5-dihydroxybenzenesulfonic acid for 2 weeks (B, b) and after this 4-week-treatment (C, c). There is a reduction of the actinic keratosis after two weeks of treatment, and a more noticeable lightening of the lesion after 4 weeks of treatment.
Figure 5:
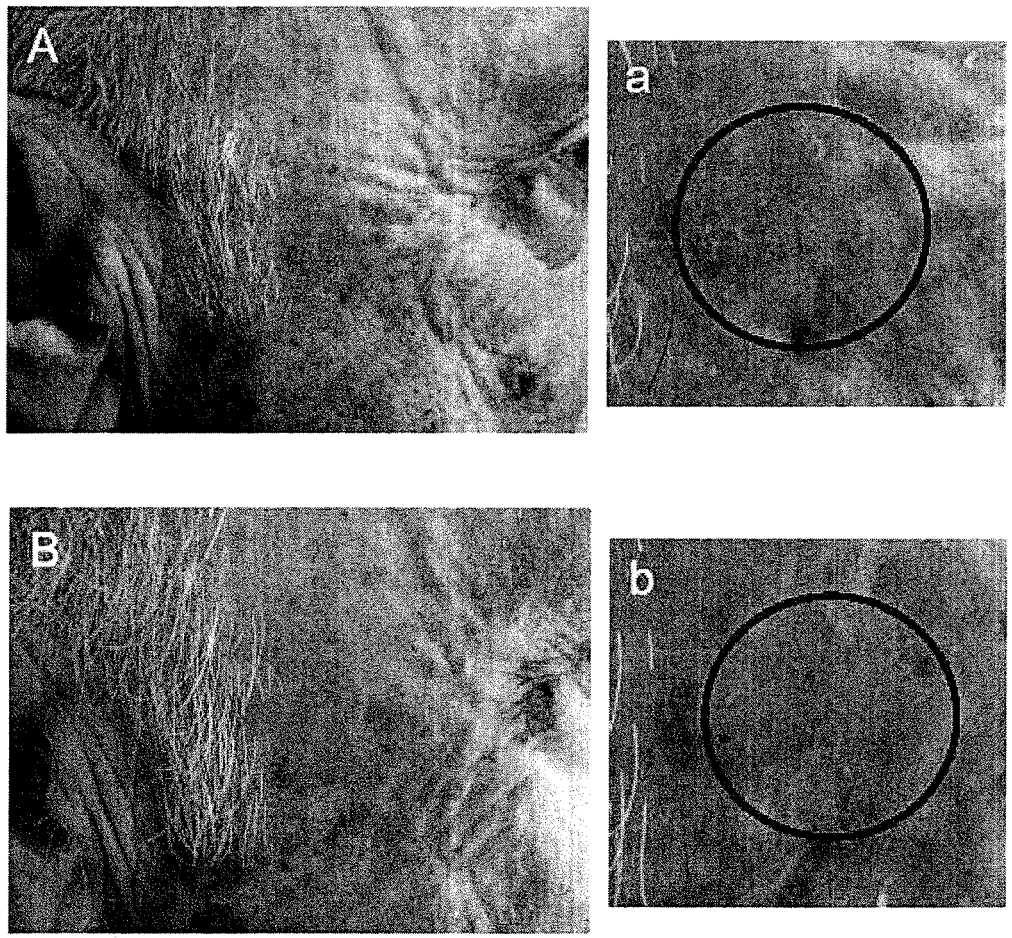
FIG. 5. Appearance of a different lesion of actinic keratosis in the same patient as in FIG. 4, before being treated (A, a) and after topical treatment of the affected skin area with an emulsion containing 2.5% 2,5-dihydroxybenzenesulfonic acid for 4 weeks (B, b). In this lesion, there is also a clear recovery as a result of the treatment.

The emulsion containing 2.5% by weight of 2,5-dihydroxybenzenesulfonic acid was also used to treat two lesions of actinic keratosis in the same patient, as shown in FIGS. 4 and 5. After 15 days of treatment with said emulsion (twice a day), the actinic keratosis was clearly reduced, and the effect was even more evident after 4 weeks of treatment.

Example 3

Effect of an emulsion of 2.5% 2,5-dihydroxybenzenesulfonate on actinic keratosis An emulsion containing 2.5% by weight of 2,5-dihydroxybenzenesulfonic acid was used to treat two lesions of actinic keratosis in the same patient, as shown in FIGS. 4 and 5. After 15 days of treatment with said emulsion (twice a day), the actinic keratosis was clearly reduced, and the effect was even more evident after 4 weeks of treatment. Calcium salt of 2,5-dihydroxybenzenesulfonic acid was used.

Example 4

Effect of a cream of 5% 2,5-dihydroxybenzenesulfonate on actinic keratosis

In this study, 2,5-dihydroxybenzenesulfonic acid, potassium salt, formulated as 5% by weight in the form of cream has been used, since this type of formulation is a habitual procedure for topical treatments of the skin. Distilled water has been used as the aqueous phase of the cream. The oil phase thereof may comprise cetyl alcohol, stearyl alcohol or vaseline. Span (sorbitan monooleate) is an effective emulsifier to make the cream.

The following example illustrates the formulation of an effective cream for the topical treatment of skin photoaging and must not be construed as a limitation of the scope of the invention.

Active principle: 2,5-dihydroxybenzenesulfonic acid, potassium salt, 5% by weight.

Excipients: cetyl alcohol (2.5%), stearyl alcohol (2.5%), liquid vaseline (30%), white soft vaseline (20%), sorbitan monooleate (5%) and distilled water (q.s. to 100 g).

Figure 6:
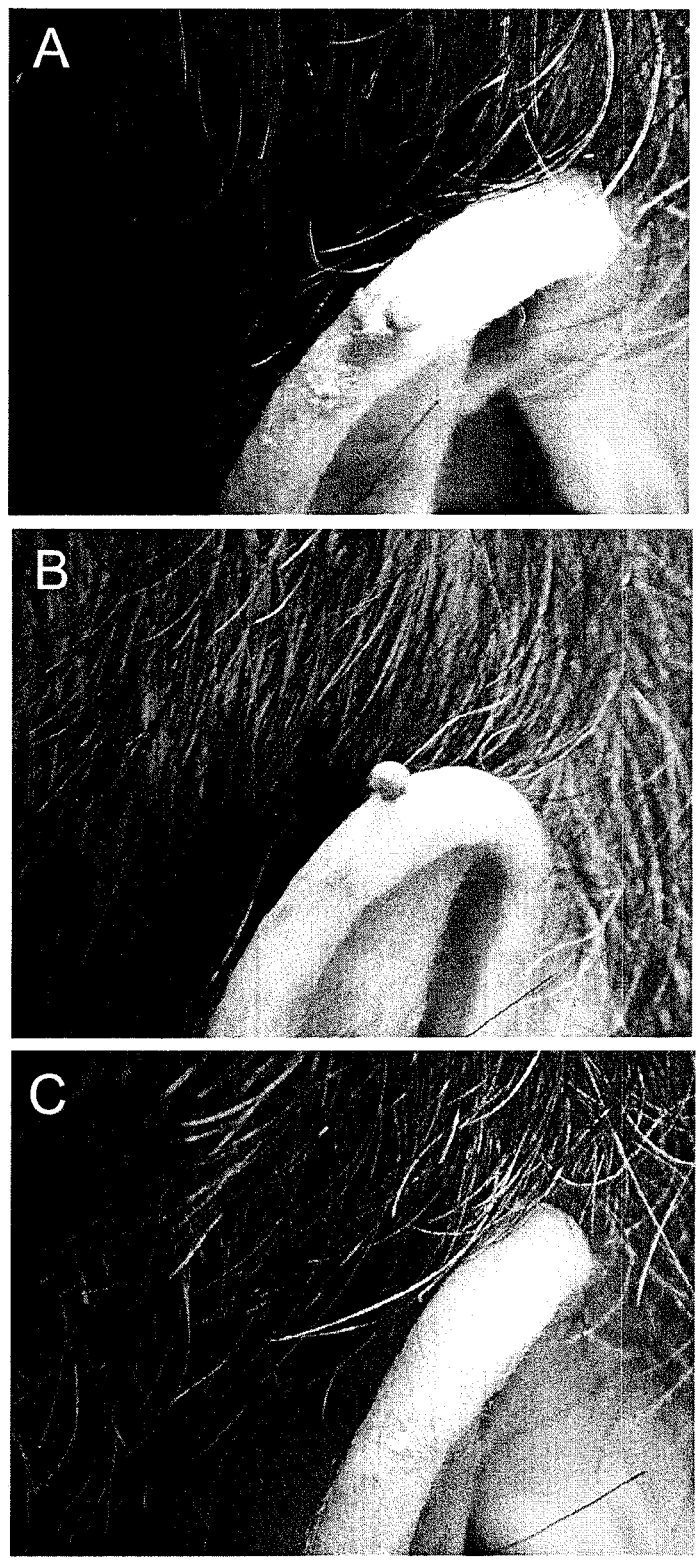
FIG. 6. Appearance of a lesion of actinic keratosis in the ear of a patient before being treated (A), after 12 days of topical treatment of the affected skin area with a cream containing 5% 2,5-dihydroxybenzenesulfonic (B) and after 15 days with this treatment (C). There is a reduction of the actinic keratosis after 12 days of treatment, and the lesion was cleared after 15 days of treatment.
Figure 7:
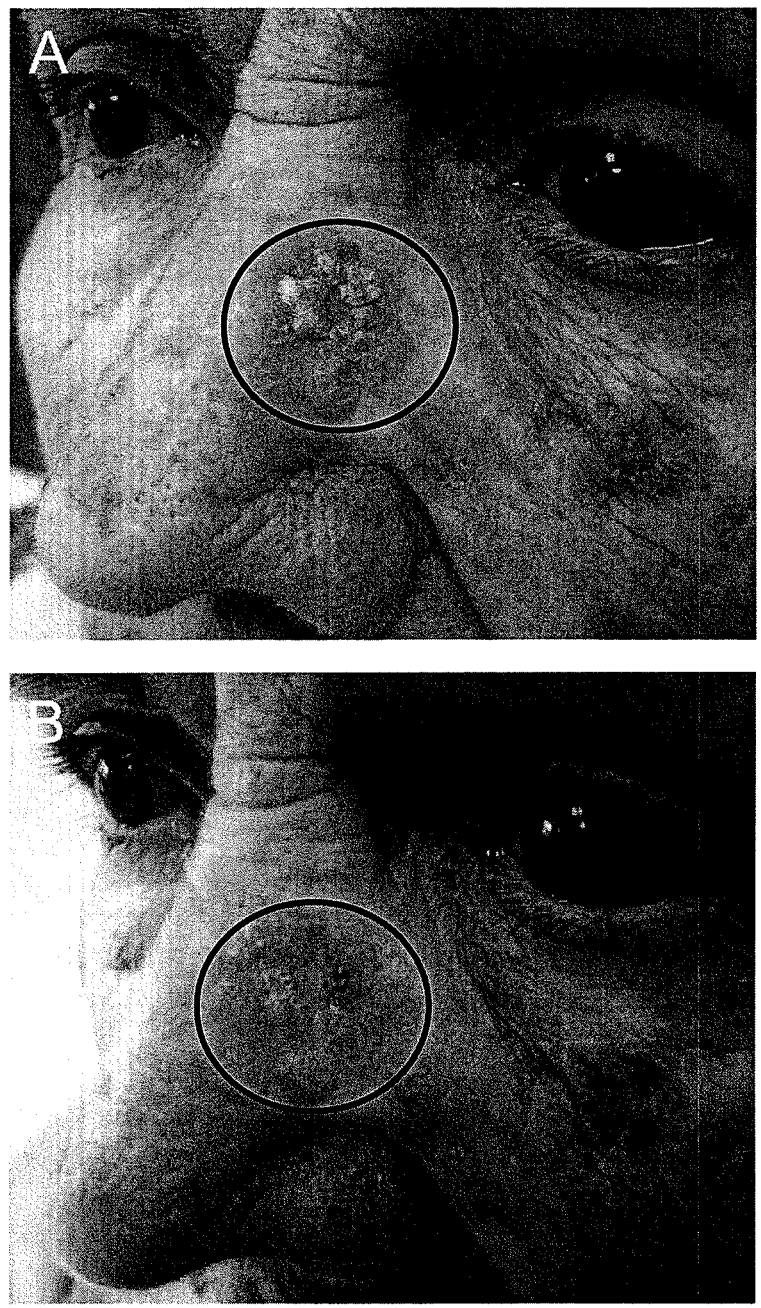
FIG. 7. Appearance of a lesion of actinic keratosis in the nose of a patient before being treated (A), and after 30 days of topical treatment of the affected skin area with a cream containing 5% 2,5-dihydroxybenzenesulfonate (B). There is a reduction of the actinic keratosis after 30 days of treatment. Circle delimitates the treated area.

The mentioned formulation was topically applied to actinic keratosis lesions in two different patients, demonstrating the efficacy of the cream containing 5% 2,5-dihydroxybenzenesulfonate to treat actinic keratosis (FIGS. 6 and 7).

Example 5

Effect of 2,5-dihydroxybenzenesulfonic acid on hair growth 2,5-dihydroxybenzenesulfonic acid, potassium salt, formulated in the form of cream was used and its composition was the same as that used in example 1.

Figure 8:
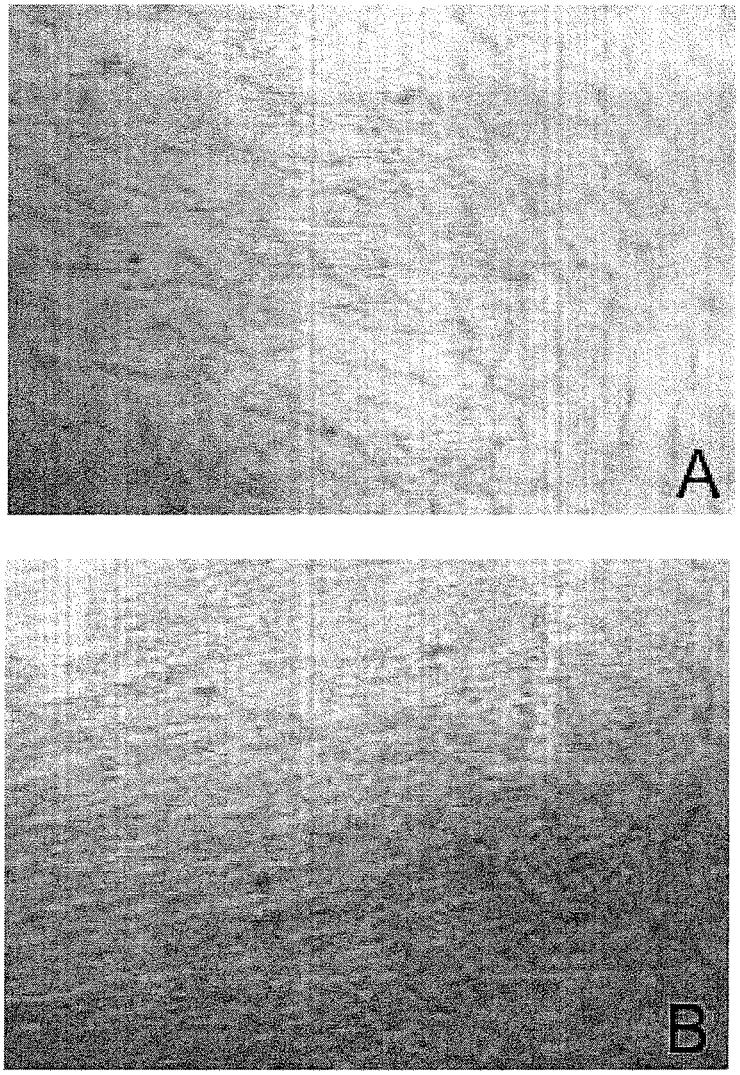
FIG. 8. Appearance of skin before treatment (A) and after topical treatment for 2 months with a cream containing 5% of 2,5-dihydroxybenzensulfonic acid (B). In image A, pilosity is more abundant than in image B.

As shown in FIG. 8B, the continuous topical treatment with this cream (twice a day for 3 months) results in the disappearance of hair in the area of application.

Example 6

Effect of the 2,5-dihydroxybenzenesulfonic acid on solar lentigos

Figure 9:
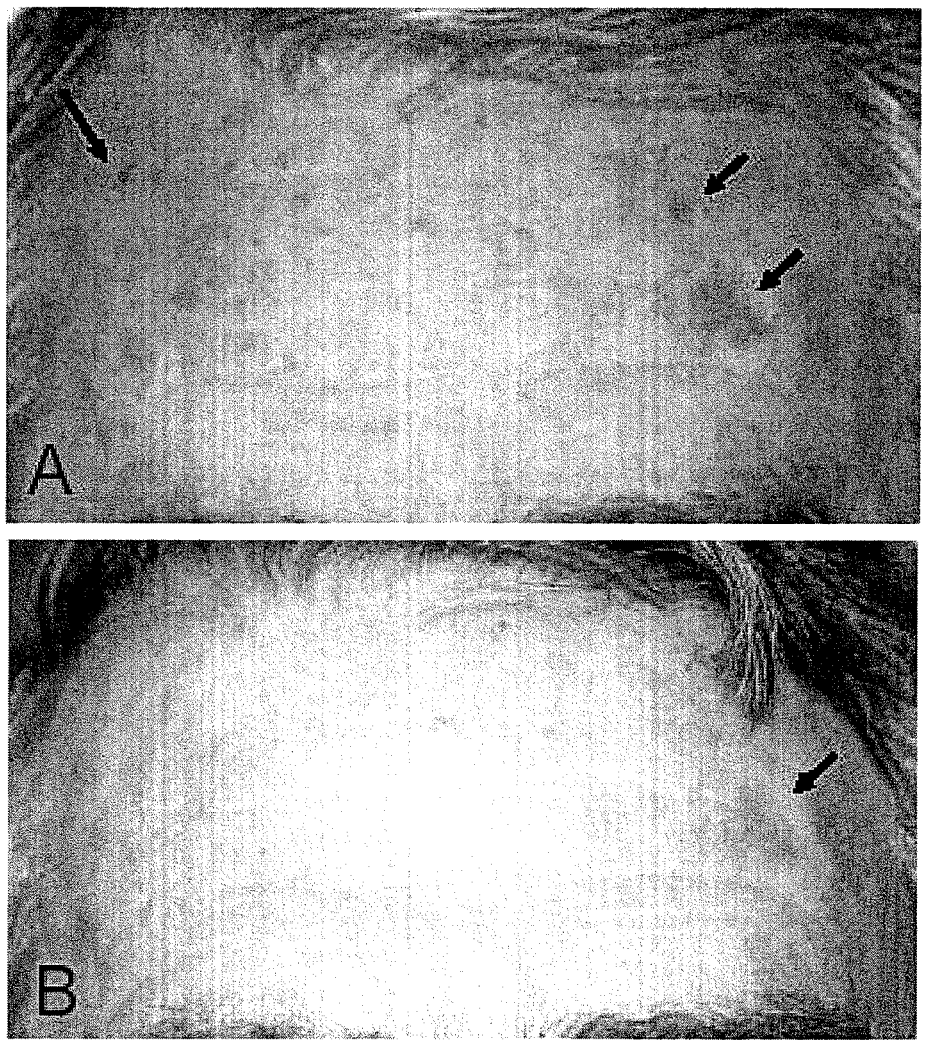
FIG. 9. Reversal of solar lentigos after treatment for two weeks with cream containing 5% 2,5-dihydroxybenzenesulfonic acid (DHBS). A, before treatment. B, after treatment.

The 2,5-dihydroxybenzenesulfonic (DHBS; 5%) cream described in example 1 was used for the topical treatment of solar lentigos in a patient. As shown in FIG. 9, after a two week treatment with DHBS in the form of cream there is a reversal of the solar lentigos.

Example 7

Assay of the 2,5-dihydroxybenzenesulfonic acid for adipogenesis

In order to demonstrate the new antiadipogenic mechanism of 2,5-dihydroxybenzenesulfonic acid we have used the cell line of preadipocytes 3T3L1. The preadipocytes were seeded in a 6 well plate where they grew up to the confluence In a standard culture médium [Dulbecco's Essential Medium (DEM)], supplemented with 1.5 g/L of sodium bicarbonate, non essential aminoacids and 10% bovine fetal serum. 2,5-dihydroxybenzenesulfonic acid (25 µM) was added to the culture medium of three wells. The culture medium was renewed every two days. After seven days, the differentiation to adipocytes was initiated in the six wells by the addition of dexametasone (250 µM), 3-isobutyl-1-methylxanthine (0.5 mM) and insuline (160 nM) during two days, followed by the substitution of the culture medium by another culture medium containing insuline (160 nM) during five days: The treatment with 2,5-dihydroxybenzenesulfonic acid (25 µM) was maintained in three wells. The culture medium was renewed every two days.

12 days later, the adipogenesis was determined by staining with Oil Red O to check the cytoplasmic accumulation of triglycerides. The cells were washed with phosphate buffer (PBS), fixed with 4% paraformaldehyde and stained during thirty minutes with Oil Red O. Isopropanol was used to remove the dye from the cells to quantify the accumulation of lipids; the absorbance thereof was measured at 510 nm in a spectrophotometer.

Figure 10:
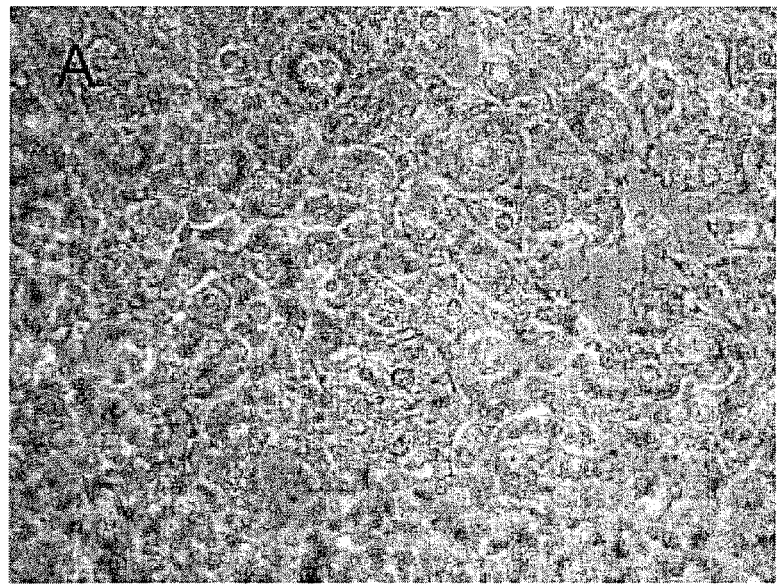
FIG. 10. Photograph A corresponds to a control culture where most of the cells are adipocytes containing triglyceride deposits. Photo B shows a culture treated with 2,5-dihydroxybenzenesulfonic acid (DHBS). Most of these cells treated with DHBS exhibit a non-differentiated (pre-adipocytes) appearance with scarce accumulation of triglycerides in the cytoplasm.
Figure 10:
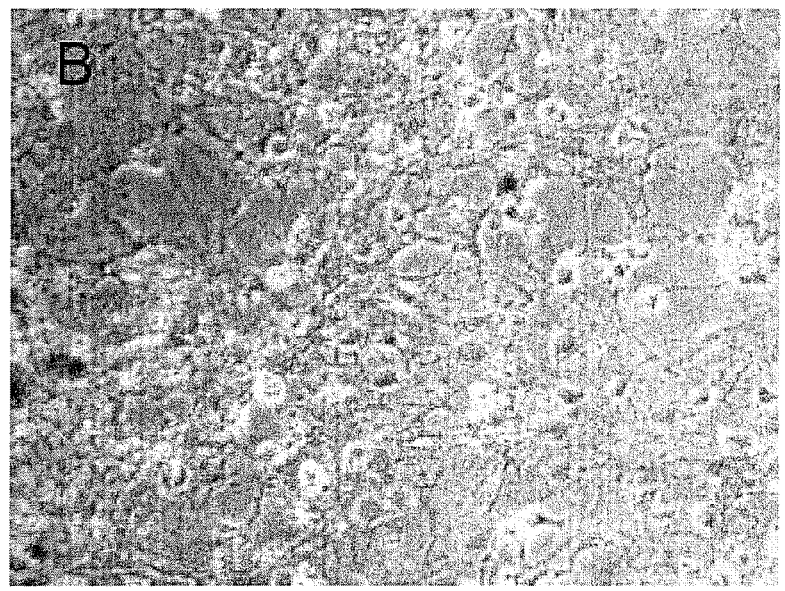
Figure 11:
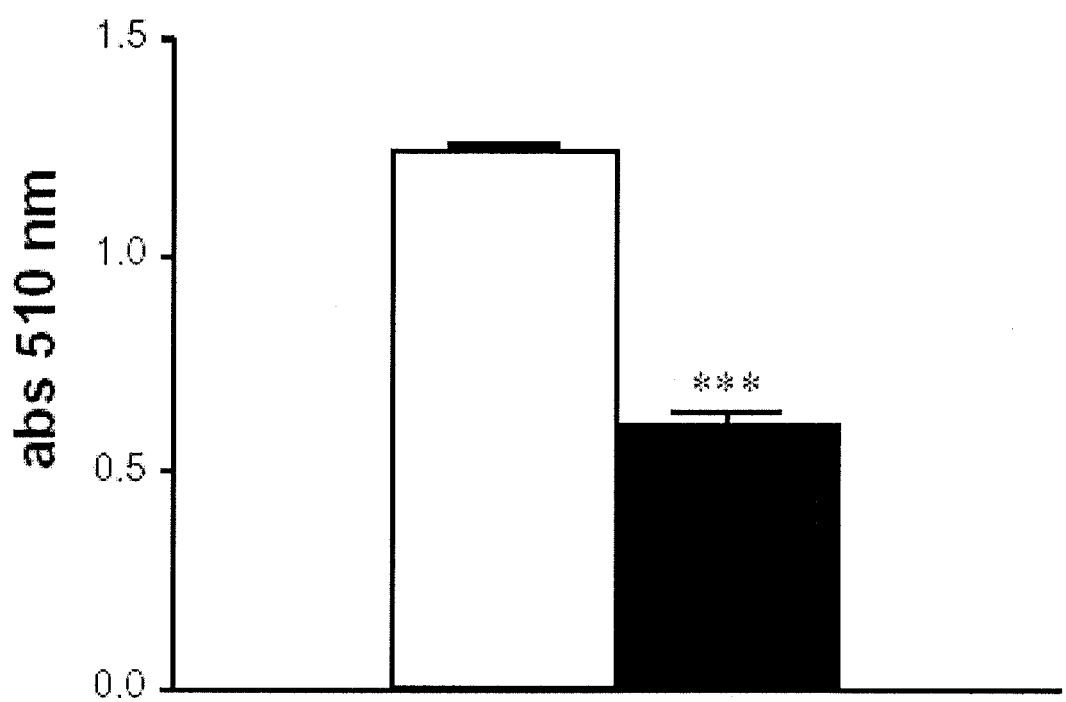
FIG. 11. Represents a histogram corresponding to the quantification of triglycerides (spectrophotometrically detected by the Oil Red 0 absorbance) in three control cultures and in three cultures of preadipocytes treated with 2,5-dihydroxybenzenesulfonic acid (DHBS, 25 µM). Ordinates: absorbance at 510 nm. The accumulation of triglycerides in the cells treated with DHBS (black bar) is significantly smaller than in the untreated cells (control) (white bar), *** $p<0.001$.

When 3T3-L1 cells (preadipocytes) are treated with 2,5-dihydroxybenzenesulfonic acid (25 µM) during 12 hours, there is a very significant reduction in the number of preadipocytes differentiated in adipocytes, as shown in FIG. 10. FIG. 10A corresponds to a control culture wherein most of the cells are adipocytes containing triglyceride deposits. FIG. 10B shows a culture treated with 2,5-dihydroxybenzenesulfonic acid. Most of these cells exhibit a non-differentiated (pre-adipocytes) aspect with scarce accumulation of triglycerides in the cytoplasm. FIG. 11 represents an histogram corresponding to the quantification of triglycerides (spectrophotometrically identified by the Oil Red O absorbance) in three control cultures and in three cultures treated with the 2,5-dihydroxybenzensulfonic compound.

This example evidences that the 2,5-dihydroxybenzene derivatives significantly inhibit adipogenesis.

Example 8

Assay of 2,5-dihydroxybenzoic acid for adipogenesis

Figure 12:
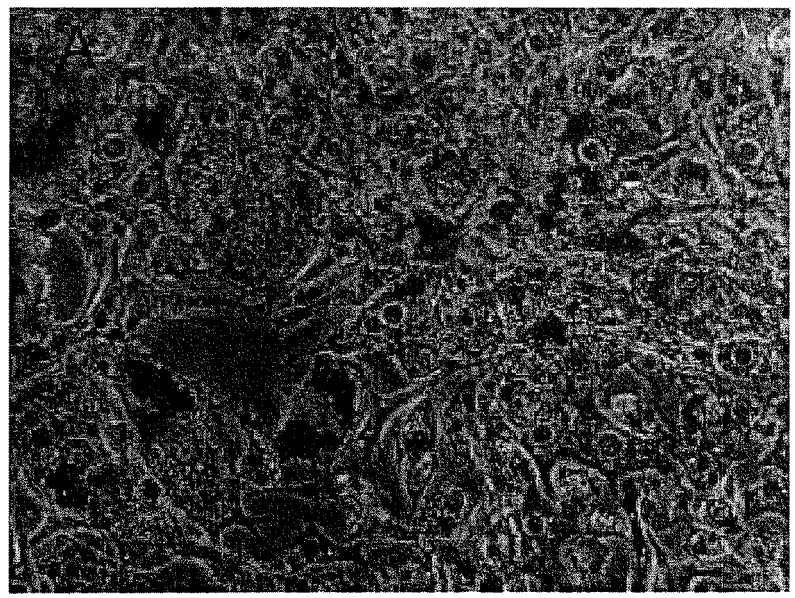
FIG. 12. Inhibition of the differentiation between pre-adipocytes and the adipogenesis by the gentisic acid (2,5-dihydroxybenzoate; 50 µM). Photograph A is the control and photograph B is the result of the treatment with gentisic acid for two weeks.
Figure 12:
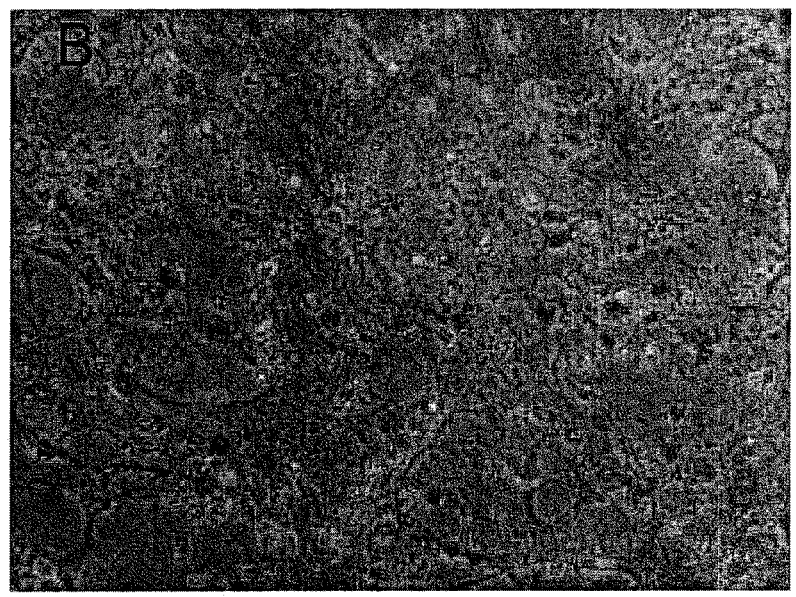

Following the same methodology explained in example 7, the effect of the gentisic acid (2,5-dihydroxybenzoic; 50 µM) was evaluated over the differentiation of the preadipocytes and the adipogenesis. In FIG. 12, the photo on the left is the control culture and the one on the right shows the 3T3-L1 preadipocytes treated with gentisic acid during two weeks. The gentisic acid inhibits the differentiation of the preadipocytes and the adipogenesis.

Figure 13:
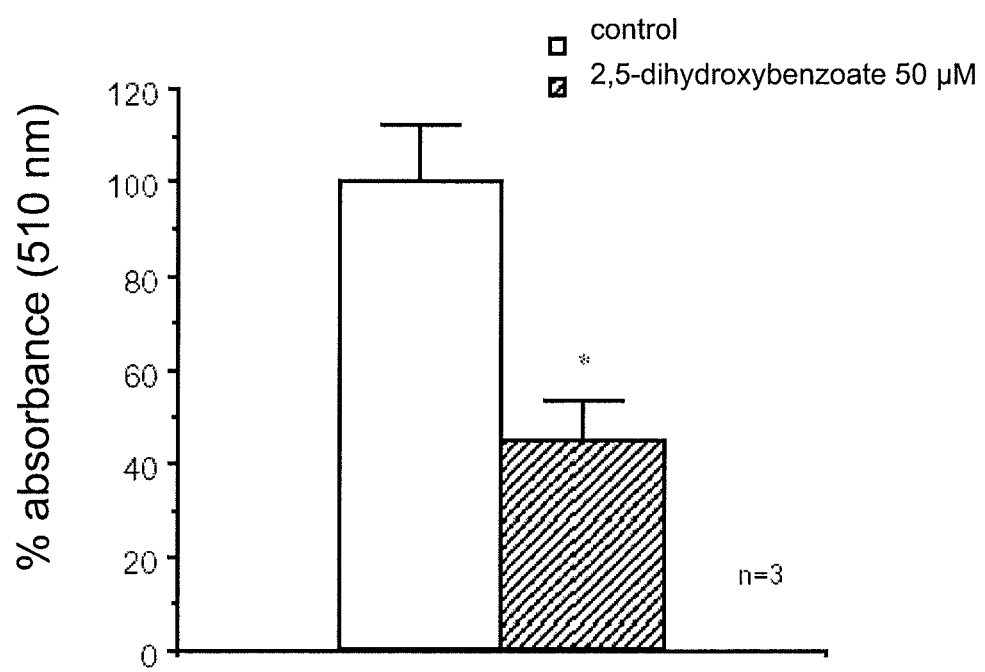
FIG. 13. Inhibition of the differentiation between pre-adipocytes and the adipogenesis by the gentisic acid (2,5-dihydroxybenzoate; 50 µM). The axis Y represents the percentage of absorbance at 510 nm. The accumulation of triglycerides in the cells treated with 2,5-dihydroxybenzoate (stripped bar) is significantly smaller than in the untreated cells (control) (white bar), *$p<0.05$.

In FIG. 13, the quantification of triglycerides (spectrophotometrically identified by the absorbance of Oil Red O) clearly demonstrates that the gentisic acid inhibits the differentiation of preadipocytes to adipocytes as well as the adipogenesis since it avoids the accumulation of lipids in the cells.

Example 9

Inhibition of the Proliferation of Preadipocytes of Subcutaneous Fat

In the adipogenesis, besides the differentiation capacity of the preadipocytes in the cells capable of storing lipids, also matters the proliferative capacity of the preadipocytes before converting into differentiated cells. Therefore, we assessed the effect of hydroxybenzene derivatives on rabbit subcutaneous fat preadipocyte proliferation was assessed.

The primary cultures of rabbit preadipocytes were obtained from the inguinal fat of New Zealand rabbits. Once the fat is removed, it is processed by mechanical disaggregation and enzymatic digestion with 0.075% type I collagenase (Gibco BRL, Paisley, Scotland, RU) for 30 minutes at 37°. The mature adipocytes are separated, removed by centrifugation (300×g, 5 min) and the cell sediment is selected. Then, the mononuclear cells with low cell density are isolated by density gradient centrifugation with Ficoll-Paque (Amersham Biosciences, Uppsala, Sweden). Once the low density mononuclear cells are obtained, they are seeded in a 75 cm$^2$ culture flask and cultured in an incubator at 37° C. with air containing 5% $CO_2$, in an Eagle medium modified by Dulbecco (DMEM) (Gibco) with 10% of bovine fetal serum (Gibco) and 0.1% of antibiotic-antimitotic (Gibco). The culture medium is replaced 24 hours later to remove the cells present in the supernatant, and to select the cells adhered to the culture flask. Then, the medium is changed every 4 days until de culture grows up to 70-80% confluence; at that moment the cells are taken off with 0.05% (w/w) trypsin (Sigma) in Hank's balanced salt solution (HBSS) (Sigma), to obtain subcultures for cell expansion. Once the subcultures reach passages 2-3, they are used to carry out experiments or they are frozen in aliquots of liquid nitrogen for later use.

The rabbit preadipocytes proliferation experiments were carried out in 24-well plates. Por this purpose, 2×10$^4$ cells were seeded per well and they were treated with vehicle, 2,5-dihydroxybenzenesulfonic (DHBS; 10 to 100 µM) or 2-acetoxy-5-hydroxybenzenesulfonic (2A-5HBS; 10 to 500 µM). The proliferation of preadipocytes was evaluated 72 hours later, and at that moment the cells were fixed with 1% glutaraldehyde. The cellular proliferation was evaluated using the crystal violet method, by measuring the absorbance at a wave length of 595 nm.

Figure 14:
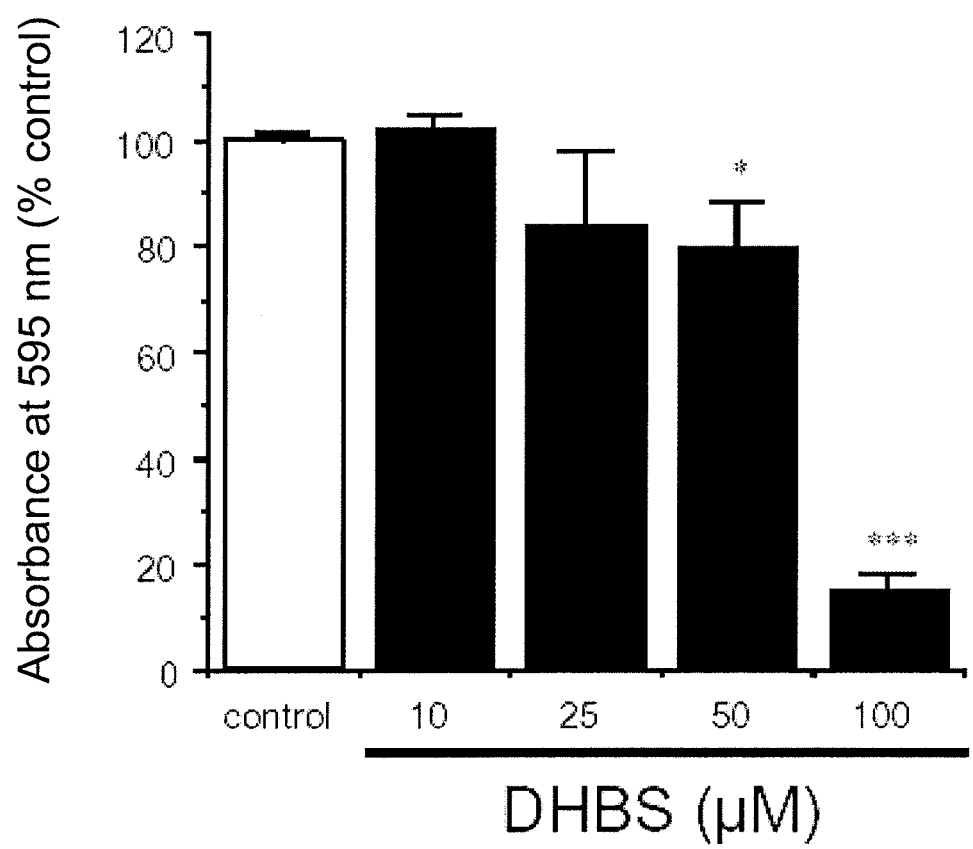
FIG. 14. Inhibition of the proliferation of preadipocytes by 2,5-dihydroxybenzenesulfonic acid (DHBS). DHBS was administered or not (control) after seeding subcutaneous fat pre-adipocytes belonging to a rabbit in 24 well plates ($10^4$ per well) until they were fixed 72 hours later. Data is expressed as the mean±SEM of the percentage of absorbance at 595 nm obtained in control cultures, which is proportional to the number of cells stained with crystal violet. Data were obtained from 3 cultures for each treatment. The white bar represents the control, whereas the black bars represent the percentage in presence of DHBS (10 to 100 µM). * indicates $p<0.05$, ***$p<0.001$ regarding control through a one-factor analysis of variance (ANOVA) of a factor followed by a Student-Newmann-Keuls post-analysis.
Figure 15:
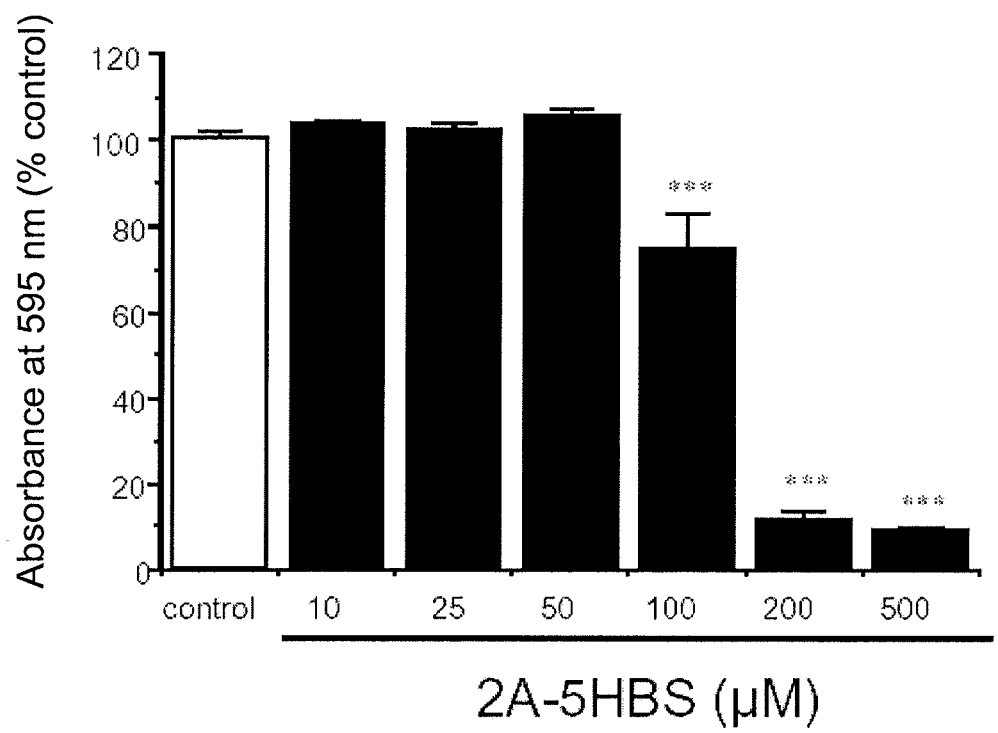
FIG. 15. Inhibition of the proliferation of pre-adipocytes by 2-acetoxy-5-hydroxybenzenesulfonic acid (2A-5HBS). 2A-5HBS was administered or not (control) after seeding subcutaneous fat pre-adipocytes belonging to a rabbit in 24 well plates ($10^4$ per well) until they were fixed 72 hours later. Data is expressed as the mean±SEM of the percentage of absorbance at 595 nm obtained in control cultures, which is proportional to the number of cells stained with crystal violet. Data were obtained from 3 cultures for each treatment. The white bar represents the control, whereas the black bars represent the percentage in presence of 2A-5HBS (10a 500 µM). *** indicates $p<0.001$ regarding control through a one-factor analysis of variance (ANOVA) followed by a Student-Newmann-Keuls post-analysis.

The DHBS and 2A-5HBS significantly inhibited the proliferation of preadipocytes obtained from subcutaneous fat of the rabbit (FIGS. 14 and 15). The effects were dependent on the concentration, obtaining a significant effect as of 50 µM for DHBS (FIG. 14) and as of 100 µM for 2A-5HBS (FIG. 15).

Surprisingly, as the following examples illustrate, in addition to FIG. 15 of example 9, in certain embodiments, the esters of 2,5-dihydroxybenzene sulfonate described in the present invention exert pharmacological actions of interest in the present invention by themselves, without needing to be first converted into 2,5-dihydroxybenzenesulfonate in order to exert such actions.

Example 10

Inhibition of Fibroblasts Mitogenesis Induced by the Fibroblast Growth Factor-1 (FGF-1)

Figure 16:
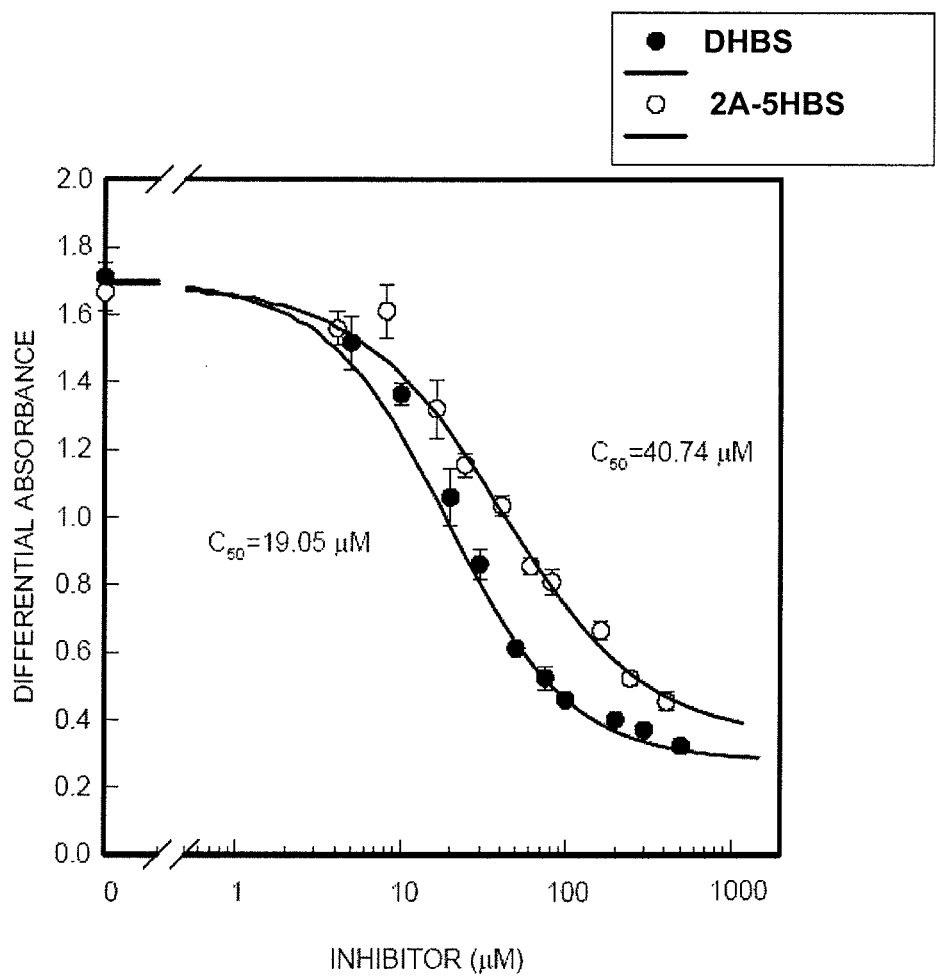
FIG. 16. Inhibition of the mitogenesis induced by fibroblast growth factor-1 in Balb/c 3T3 fibroblast quiescent cultures by calcium 2-acetoxy-5-hydroxybenzenesulfonate (2A-5HBS) and potassium 2,5-dihydroxybenzenesulfonate (DHBS).
Figure 17:
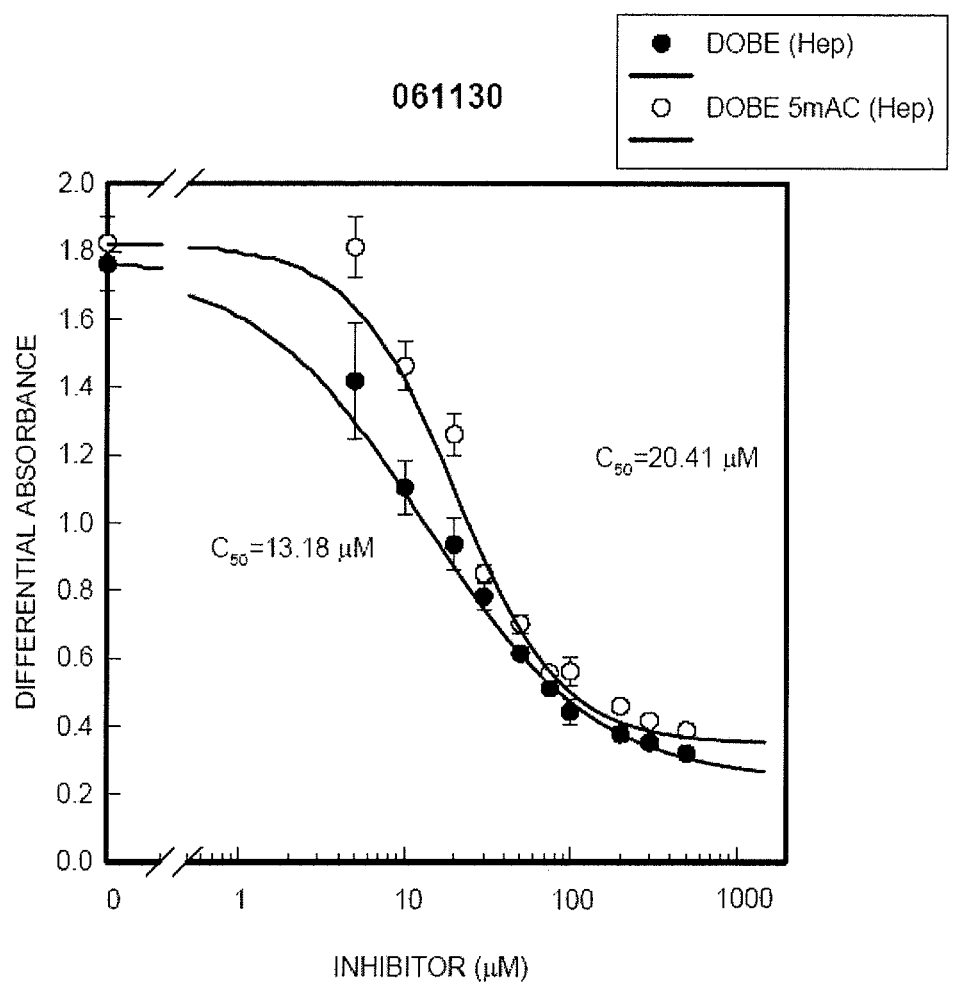
FIG. 17. Inhibition of the mitogenesis induced by fibroblast growth factor-1 in Balb/c 3T3 fibroblast quiescent cultures by potassium 5-acetoxy-2-hydroxybenzenesulfonate (5A-2HBS) and potassium 2,5-dihydroxybenzenesulfonate (DHBS).
Figure 18:
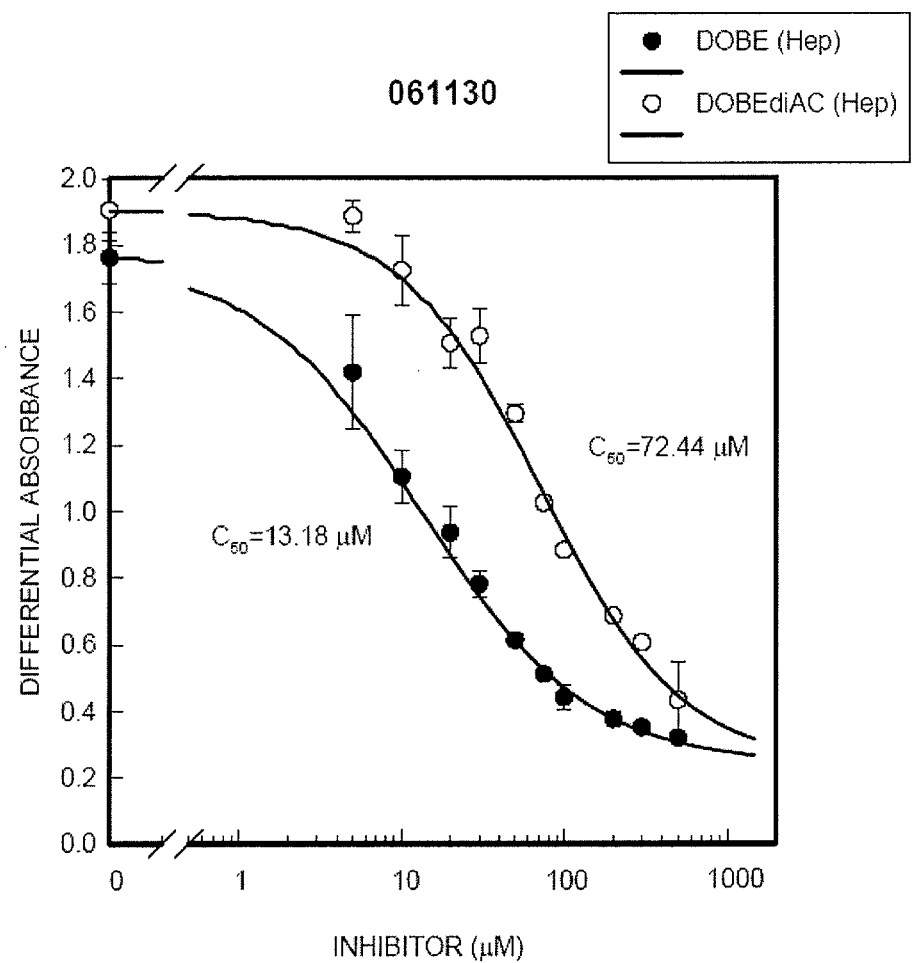
FIG. 18. Inhibition of the mitogenesis induced by fibroblast growth factor-1 in Balb/c 3T3 fibroblast quiescent cultures by potassium 2,5-diacetoxybenzene sulfonate (DABS) and potassium 2,5-dihydroxybenzene sulfonate (DHBS).

Inhibition of FGF-1 mitogenesis was observed in quiescent cultures of Balb/c 3T3 fibroblasts by 2-acetoxy-5-hydroxybenzenesulfonate (FIG. 16), 5-acetoxy-2-hydroxybenzenesulfonate (FIG. 17) and 2,5-diacetoxybenzenesulfonate (FIG. 18). The evaluated compounds were used in the form of potassium salt, except in the first case in which calcium salt was used. The experiments were carried out as described in Fernández-Tornero C et al. *J Biol Chem*, 2003.

Example 11

Effect of monoesters of 2,5-dihydroxybenzenesulfonate on the proliferation of mouse glioma C6 cells The following example shows the efficacy of the monoesters of 2,5-dihydroxybenzenesulfonic, potassium 2-acetoxy-5-hydroxybenzenesulfonate (2A-5HBS) and potassium 5-acetoxy-2-hydroxybenzenesulfonate (5A-2HBS) to reduce the proliferation capacity of glioma cells and supports the use of the compounds in the treatment of gliomas.

The cell line used was that of mouse glioma C6 cells. Once attached, the cells were treated or not treated (controls) with (5A-2HBS) (500 μM) or (2A-5HBS) (500 μM) and they were allowed to proliferate during 48 hours. After that, the proliferation of glioma cells was evaluated by staining the fixed cells with crystal violet. The number of cells is proportional to the amount of retained dye, which was spectrophotometrically determined by measuring absorbance at 595 nm after removing the dye from the cells.

Figure 19:
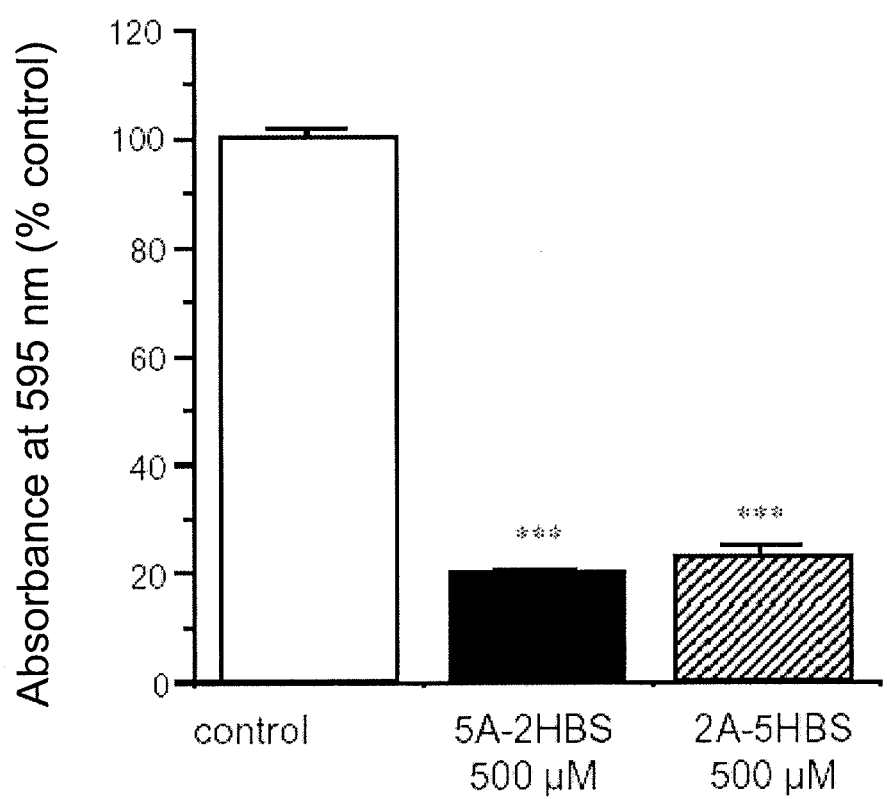
FIG. 19. Shows the effect of the treatment with potassium 5-acetoxy-2-hydroxybenzenesulfonate (5-mono acetylated dobesilate; 5A-2HBS) and the potassium 2-acetoxy-5-hydroxybenzenesulfonate (2-mono acetylated dobesilate; 2A-5HBS) on the proliferation of mouse C6 glioma cells. 5A-2HBS and 2A-5HBS were administered or not (control) after seeding C6 cells in 24 well plates ($10^4$ per well) until they were fixed 48 hours later. Data is expressed as the mean±SEM of the percentage of absorbance at 595 nm obtained in control cultures, which is proportional to the number of cells stained with crystal violet. Data were obtained from 3 cultures for each treatment and 6 control cultures. The white bar represents the value of the control cells, whereas the black bar shows the value in the presence of 5A-2HBS (500 µM), and the stripped bar shows the value in the presence of 2A-5HBS (500 µM). *** indicates p<0.001 regarding control through a one-factor analysis of variance (ANOVA) followed by a Student-Newmann-Keuls post-analysis.

Both monoesters of 2,5-dihydroxybenzenesulfonate, (5A-2HBS) and (2A-5HBS) caused the inhibition of the proliferation of mouse glioma cells (FIG. 19).

Example 12

Analysis of the structural interaction of the esters of 2,5-dihydroxybenzenesulfonate with the fibroblast growth factor-1 (FGF-1)

Figure 20:
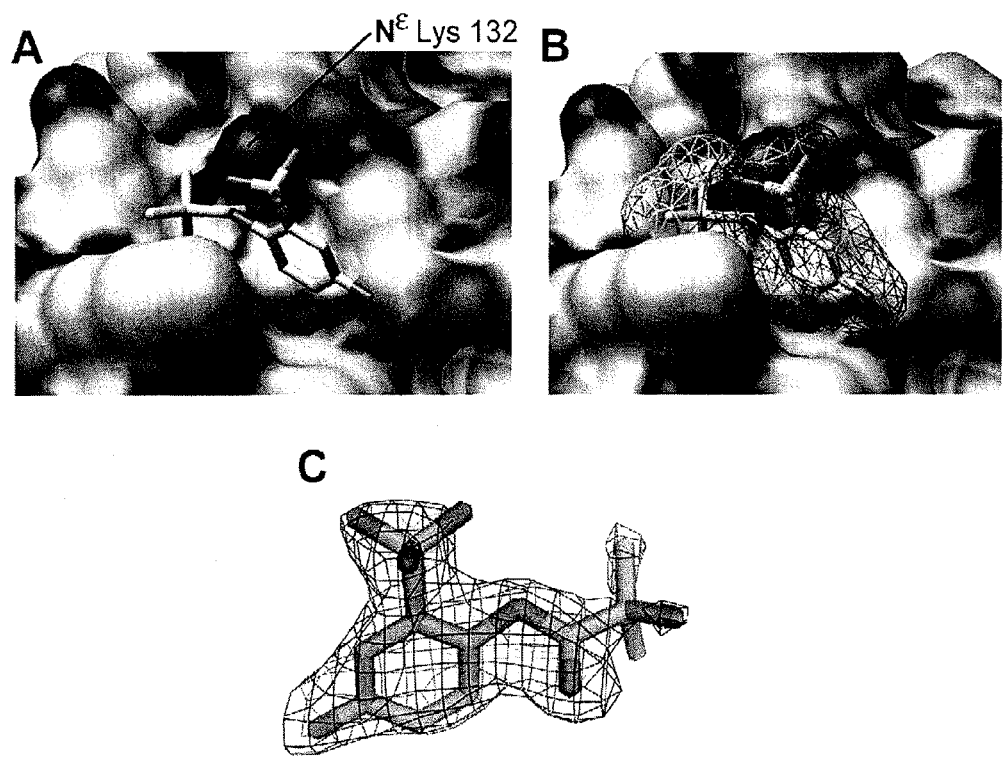
FIG. 20. Co-crystallized potassium 5-acetoxy-2-hydroxy-benzenesulfonic acid with fibroblast growth factor-1. The electron density of the compound, contoured at 1σ (panel C), enables the localization and recognition of the compound orientation regarding the protein (panels A and B), as well as the confirmation that the compound maintains the acetoxyl group in position 2 when it binds to the protein. The compound is located at a site very close to the site that, as described, is occupied by the 2,5-dihydroxybenzenesulfonic acid, which aromatic ring forms a cation-π bond with the $N^\epsilon$ group of lysine 132, marked in panel A as reference. Panel B shows, in the form of a mesh, the Van der Waals volume of 2-acetoxy-5-hydroxybenzenesulfonic acid, overlapped to its representation in the form of rods. In panels A and B, the protein surface is colored according to its electrostatic potential (light grey: negative charge; dark grey: positive charge; white: lack of charge).
Figure 21:
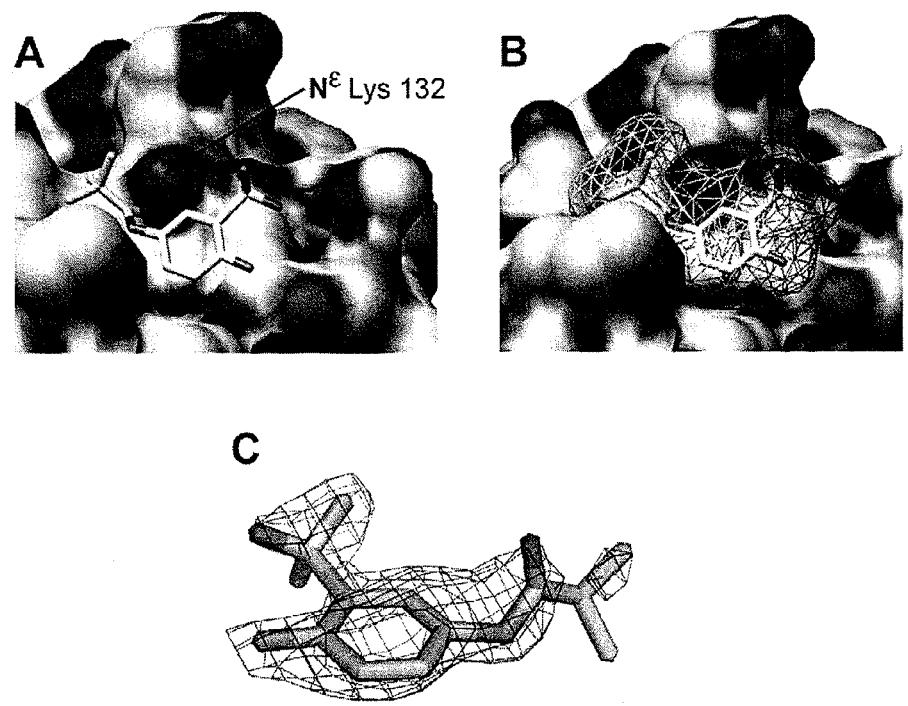
FIG. 21. Co-crystallized potassium 5-acetoxy-2-hydroxy-benzenesulfonic acid with fibroblast growth factor-1. The electron density of the compound, contoured at 1σ (panel C), enables the localization and recognition of the compound orientation regarding the protein (panels A and B) as well as the confirmation that the compound maintains the acetoxyl group in position 5 when it binds to the protein. The compound is located at a site very close to the site that, as described, is occupied by the 2,5-dihydroxybenzenesulfonic acid, which aromatic ring forms a cation-π bond with the $N^\epsilon$ group of lysine 132, marked in panel A as reference. Panel B shows, in the form of a mesh, the Van der Waals volume of 2-acetoxy-5-hydroxybenzenesulfonic acid, overlapped to its representation in the form of rods. In panels A and B, the protein surface is colored according to its electrostatic potential (light grey: negative charge; dark grey: positive charge; white: lack of charge).
Figure 22:
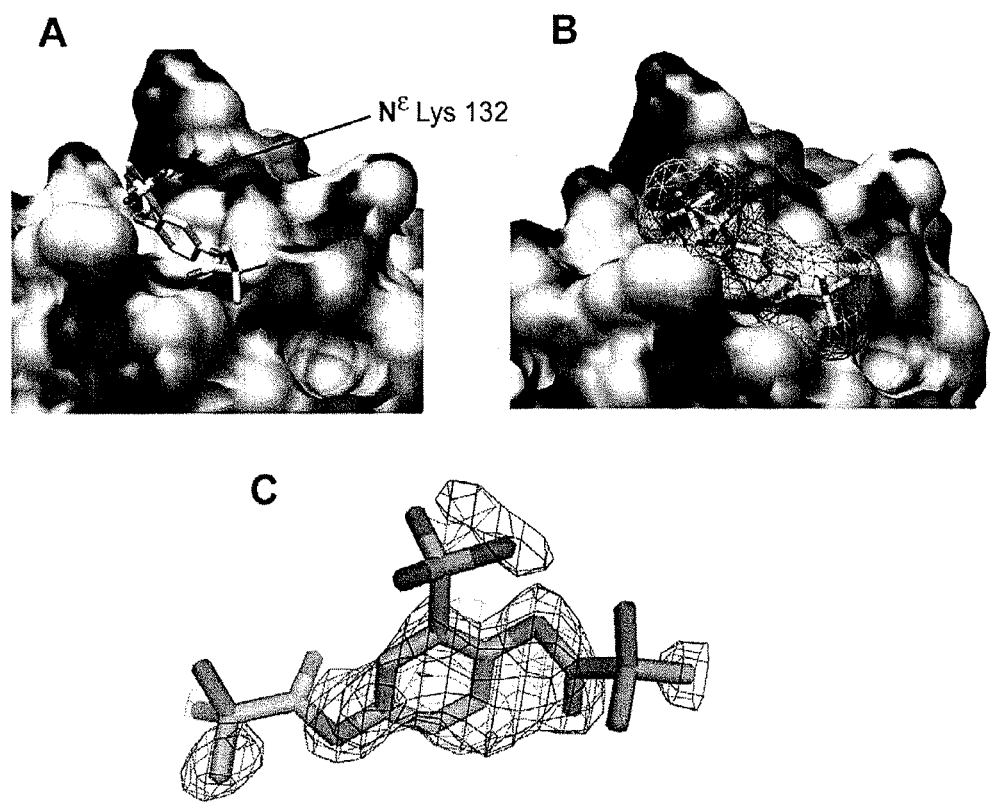
FIG. 22. Co-crystallized 2,5-diacetoxybenzenesulfonic acid with fibroblast growth factor-1. The electron density of the compound, contoured at 1σ (panel C), enables the localization and recognition of the compound orientation regarding the protein (panels A and B) as well as the confirmation that the compound maintains the acetoxyl groups in positions 2 and 5 when it binds to the protein. The compound is located at a site very close to the site that, as described, is occupied by the 2,5-dihydroxybenzenesulfonic acid, which aromatic ring forms a cation-π bond with the $N^\epsilon$ group of lysine 132, marked in panel A as reference. Panel B represents, in the form of a mesh, the Van der Waals volume of 2,5-diacetoxy-benzenesulfonic acid, overlapped to its representation in the form of rods. In panels A and B, the protein surface is colored according to its electrostatic potential (light grey: negative charge; dark grey: positive charge; white: lack of charge).

As of the diffraction from complex crystals of FGF-1: 2-acetoxy-5-hydroxybenzenesulfonic acid, FGF-1: 5-acetoxy-2-hydroxybenzenesulfonic acid and FGF-1: 2,5-diacetoxybenzenesulfonic acid, the complex structures were calculated and represented. In FIGS. 20, 21 and 22, representing the surface of the protein coloured according to its electrostatic potential (light grey: negative charge, dark grey: positive charge, white: areas with no charge), the interaction form of the 2-acetoxy-5-hydroxybenzenesulfonic acid, 5-acetoxy-2-hydroxybenzenesulfonic acid and 2,5-diacetoxybenzenesulfonic acid, respectively, with the FGF-1 may be observed. The electronic density of the compound, contoured at 1σ (FIGS. 20-22, panels C), enabled the localization and determination of the orientations of the compounds regarding the protein (FIGS. 20-22, panels A and B), as well as the confirmation that the compounds keep the acetoxyl groups in positions 2, 5 and, 2 and 5, respectively, when they bind to the protein. The compounds are located at a site very close to the site that, as described, is occupied by the 2,5-dihydroxybenzenesulfonic acid, which aromatic ring forms a cation-π bond with the $N^\epsilon$ group of lysine 132, marked in FIGS. 20-22, panels A, as reference.

Each patent, patent application, and publication cited or described in the present application is hereby incorporated by reference in its entirety as if each individual patent, patent application, or publication was specifically and individually indicated to be incorporated by reference.

While specific embodiments of the subject invention have been discussed, the above specification is illustrative and not restrictive. One skilled in the art will appreciate that numerous changes and modifications can be made to the invention, and that such changes and modifications can be made without departing from the spirit and scope of the invention. The full scope of the invention should be determined by reference to the claims, along with their full scope of equivalents, and the specification, along with such variations.

The invention claimed is:

1. A method for the treatment of actinic keratosis, comprising topically administering to a subject in need thereof, an effective amount of 2,5-dihydroxybenzenesulfonic acid (Dobesilate) or a pharmaceutically acceptable salt.

2. The method of claim 1, wherein the salt is selected from the group consisting of: calcium 2,5-dihydroxybenzenesulfonate (calcium Dobesilate); potassium 2,5-dihydroxybenzenesulfonate (potassium Dobesilate); magnesium 2,5-dihydroxybenzenesulfonate (magnesium Dobesilate); diethylamine 2,5-dihydroxybenzenesulfonate (Ethamsylate).

3. The method of claim 2, wherein the salt is calcium 2,5-dihydroxybenzenesulfonate (calcium Dobesilate).

4. The method of claim 2, wherein the salt is potassium 2,5-dihydroxybenzenesulfonate (potassium Dobesilate).

5. The method of claim 1, wherein the actinic keratosis is selected from the group consisting of: hypertrophic, atrophic, bowenoid, and acantholythic keratosis.

6. The method of claim 1, wherein the compound is administered at least once per week.

7. The method of claim 6, wherein the compound is administered at least once per day.

8. The method of claim 7, wherein the compound is administered at least twice per day.

9. The method of claim 1, wherein the compound is present in a pharmaceutical composition in an amount of at least about 1% w/w.

10. The method of claim 9, wherein the compound is present in a pharmaceutical composition in an amount of at least about 2.5% w/w.

11. The method of claim 10, wherein the compound is present in a pharmaceutical composition in an amount of at least about 5% w/w.

12. The method of claim 11, wherein the compound is present in a pharmaceutical composition in an amount of at least about 10% w/w.

13. The method of claim 12, wherein the compound is present in a pharmaceutical composition in an amount of at least about 15% w/w.

14. The method of claim 1, wherein the compound is administered over a period of at least about one week.

15. The method of claim 14, wherein the compound is administered over a period of at least about four weeks.

16. The method of claim 4, wherein the potassium 2,5-dihydroxybenzenesulfonate (potassium Dobesilate) is administered as a cream at a concentration of at least about 2.5% w/w.

17. The method of claim 16, wherein the potassium 2,5-dihydroxybenzenesulfonate (potassium Dobesilate) is administered as a cream at a concentration of at least about 5% w/w.

18. The method of claim 17, wherein the cream further comprises one or more emollients and one or more emulsifiers.

19. The method of claim 16, wherein the potassium 2,5-dihydroxybenzenesulfonate (potassium Dobesilate) is administered at least twice per day over a period of at least four weeks.

20. A method for the treatment of actinic keratosis, comprising topically administering to a subject in need thereof a cream comprising 5% of potassium 2,5-dihydroxybenzenesulfonic acid (potassium Dobesilate) w/w, wherein the cream is administered at least twice per day over a period of at least four weeks.

* * * * *